(12) United States Patent
Ma et al.

(10) Patent No.: US 10,325,369 B2
(45) Date of Patent: Jun. 18, 2019

(54) METHOD AND SYSTEM FOR ANALYZING BLOOD FLOW CONDITION

(71) Applicant: SHANGHAI UNITED IMAGING HEALTHCARE CO., LTD., Shanghai (CN)

(72) Inventors: Jieyan Ma, Shanghai (CN); Yuan Ren, Shanghai (CN); Hongjian Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 84 days.

(21) Appl. No.: 15/693,375

(22) Filed: Aug. 31, 2017

(65) Prior Publication Data

US 2018/0211388 A1      Jul. 26, 2018

Related U.S. Application Data

(63) Continuation of application No. 15/498,428, filed on Apr. 26, 2017, which is a continuation of application No. PCT/CN2017/072256, filed on Jan. 23, 2017.

(51) Int. Cl.
*A61B 5/02* (2006.01)
*G06T 7/00* (2017.01)
(Continued)

(52) U.S. Cl.
CPC ............ *G06T 7/0016* (2013.01); *A61B 5/021* (2013.01); *A61B 5/02007* (2013.01);
(Continued)

(58) Field of Classification Search
CPC . G06T 7/0016; G06T 7/32; G06T 7/11; G06T 2207/30101; G06T 2207/30104; A61B 5/02007; A61B 5/021
See application file for complete search history.

(56) References Cited

U.S. PATENT DOCUMENTS 9,042,613 B2    5/2015  Spilker et al.
9,119,540 B2    9/2015  Sharma
(Continued)

FOREIGN PATENT DOCUMENTS

CN    105096388 A    11/2015
CN    106327487 A    1/2017
(Continued)

OTHER PUBLICATIONS

C.A. Taylor & D.A. Steinman, Image-Based Modeling of Blood Flow and Vessel Wall Dynamics: Applications, Methods and Future Directions. Annals of Biomedical Engineering, 38(3):1188-1203, 2010.
(Continued)

*Primary Examiner* — Kim Y Vu
*Assistant Examiner* — Molly Delaney
(74) *Attorney, Agent, or Firm* — Metis IP LLC

(57) ABSTRACT

The present application relates to a method and system for analyzing blood flow conditions. The method includes: obtaining images at multiple time phases; constructing multiple vascular models corresponding to the multiple time phases; correlating the multiple vascular models; setting boundary conditions of the multiple vascular models respectively based on the result of correlation; and determining condition of blood vessel of the vascular models.

20 Claims, 16 Drawing Sheets

(51) Int. Cl.
*G06T 7/11* (2017.01)
*G06T 7/32* (2017.01)
*A61B 5/021* (2006.01)
*G16H 10/00* (2018.01)
*G16H 50/50* (2018.01)
*A61B 5/0285* (2006.01)

(52) U.S. Cl.
CPC .............. *A61B 5/0285* (2013.01); *G06T 7/11* (2017.01); *G06T 7/32* (2017.01); *G16H 10/00* (2018.01); *G16H 50/50* (2018.01); *G06T 2207/30101* (2013.01); *G06T 2207/30104* (2013.01)

(56) References Cited

U.S. PATENT DOCUMENTS

| | | |
|---|---|---|
| 9,141,763 B2 | 9/2015 | Sharma et al. |
| 9,390,232 B2 | 7/2016 | Taylor et al. |
| 9,449,147 B2 | 9/2016 | Taylor |
| 9,724,164 B2 | 8/2017 | Yagi et al. |
| 2012/0022843 A1 | 1/2012 | Ionasec |
| 2012/0203530 A1 | 8/2012 | Sharma et al. |
| 2012/0207366 A1 | 8/2012 | Liu |
| 2013/0132054 A1 | 5/2013 | Sharma et al. |
| 2013/0243294 A1* | 9/2013 | Ralovich ............... G06T 7/0012 382/131 |
| 2014/0058715 A1 | 2/2014 | Sharma et al. |
| 2014/0073977 A1 | 3/2014 | Grady et al. |
| 2014/0328462 A1 | 11/2014 | Uehara |
| 2015/0038860 A1 | 2/2015 | Fonte et al. |
| 2015/0112182 A1* | 4/2015 | Sharma ................ A61B 5/0261 600/408 |
| 2015/0112191 A1 | 4/2015 | Gilboa et al. |
| 2015/0245776 A1 | 9/2015 | Hirohata et al. |
| 2015/0262357 A1 | 9/2015 | Igarashi et al. |
| 2015/0269349 A1* | 9/2015 | Taylor ................ G06F 17/5009 703/11 |
| 2015/0282765 A1 | 10/2015 | Goshen et al. |
| 2015/0317429 A1 | 11/2015 | Peters et al. |
| 2015/0356734 A1 | 12/2015 | Ooga et al. |
| 2015/0359601 A1 | 12/2015 | Sauer |
| 2016/0117816 A1 | 4/2016 | Heartflow et al. |
| 2016/0133015 A1 | 5/2016 | Taylor |
| 2016/0206260 A1 | 7/2016 | Wakai et al. |
| 2016/0232667 A1 | 8/2016 | Taylor |
| 2016/0267654 A1 | 9/2016 | Wang |
| 2016/0306943 A1 | 10/2016 | Choi et al. |
| 2017/0071479 A1* | 3/2017 | Kano ................. A61B 5/02007 |
| 2017/0105694 A1 | 4/2017 | Grass et al. |
| 2017/0202621 A1 | 7/2017 | Taylor |

FOREIGN PATENT DOCUMENTS

| | | |
|---|---|---|
| CN | 105513036 A | 4/2018 |
| EP | 3188059 A1 | 7/2017 |
| JP | 2015097759 A | 5/2015 |
| WO | 2012021307 A2 | 2/2012 |
| WO | 2015058044 A1 | 4/2015 |
| WO | 2016008837 A1 | 1/2016 |

OTHER PUBLICATIONS

C.A. Taylor et al., Computational Fluid Dynamics Applied to Cardiac Computed Tomography for Noninvasive Quantification of Fractional Flow Reserve. Journal of the American College of Cardiology, 61(22):2233-2241, 2013.

S.-S. Kwon et al., A novel patient-specific model to compute coronary fractional flow reserve. Progress in Biophysics and Molecular Biology, 116:48-55, 2014.

C. Kirbas & F. Quek. A review of vessel extraction techniques and algorithms. ACM Comp. Surv.,36(2):81-121, 2004.

O. Wink et al., Fast delineation and visualization of vessels in 3-d angiographic images. IEEE Trans. Med. Im., 19 (4):337-346, 2000.

O. Wink et al. Multiscale vessel tracking. IEEE Trans. Med. Im., 23(1):130-133, 2004.

M.F. Fillinger et al., In vivo analysis of mechanical wall stress and abdominal aortic aneurysm rupture risk. Forty-ninth Annual Meeting of the American Association for Vascular Surgery, Baltimore, Md, Jun. 12-13, 2001.

J. Ma & A. Turan, Pulsatile Non-Newtonian Haemodynamics in a 3D Bifurcating Abdominal Aortic Aneurysm Model, Computer Methods in Biomechanics and Biomedical Engineering, 14(8):683-694, 2011.

B. Moore et al., 3D models of blood flow in the cerebral vasculature. Journal of Biomechanics, 39(8): 1454-1463, 2006.

J.R. Cebral et al., Blood-flow models of the circle of Willis from magnetic resonance data. Journal of Engineering Mathematics, 47(3-4): 369-386, 2003.

H. Meng et al., Complex hemodynamics at the apex of an arterial bifurcation induces vascular remodeling resembling cerebral aneurysm initiation[J]. Stroke, 38(6):1924-1931, 2007.

J.F. LaDisa et al., Stent design properties and deployment ratio influence indexes of wall shear stress: a three-dimensional computational fluid dynamics investigation within a normal artery. Journal of Applied Physiology, 97 (1):424-430, 2004.

C. L. Lawson, Software for C1 Surface interpolation. Mathematical Software III (John R. Rice, editor), Academic Press, New York. 1977, pp. 161-194.

Steven Fortune, A Sweepline Algorithm for Voronoi Diagrams. Algorithmica, 2: 153-174(1987).

D. T. Lee et al., Two Algorithms for Constructing a Delaunay Triangulation. International Journal of Computer and Information Sciences, 9(3): 219-242(1980).

P. D. Richardson et al., Influence of Plaque Configuration and Stress Distribution on Fissuring of Coronary Atherosclerotic Plaques. The Lancet, 334(8669): 941-944(1969).

Howard M. Loree et al., Effects of Fibrous Cap Thickness on Peak Circumferential Stress in Model Atherosclerotic Vessels. Circulation Research, 71(4): 850-858(1992).

George C. Cheng et al., Distribution of Circumferential Stress in Ruptured and Stable Atherosclerotic Lesions: A Structural Analysis with Histopathological Correlation. Circulation, 87(4): 1179-1187(1993).

Hayden Huang et al., The Impact of Calcification on the Biomechanical Stability of Atherosclerotic Plaques, Circulation, 103(8): 1051-1056(2001).

Liang Wang et al., IVUS-Based FSI Models for Human Coronary Plaque Progression Study: Components, Correlation and Predictive Analysis. Annals of Biomedical Engineering, 43(1): 107-121(2015).

Dalin Tang et al., Sites of Rupture in Human Atherosclerotic Carotid Plaques Are Associated With High Structural Stresses: An In Vivo MRI-Based 3D Fluid-Structure Interaction Study. Stroke, 40: 3258-3263(2009).

Dalin Tang et al., 3D MRI-Based Anisotropic FSI Models with Cyclic Bending for Human Coronary Atherosclerotic Plaque Mechanical Analysis. Journal of Biomechanical Engineering, 131(6): 1-27(2009).

Dalin Tang et al., A Negative Correlation between Human Carotid Atherosclerotic Plaque Progression and Plaque Wall Stress: in Vivo MRI-Based 2D/3D FSI Models. Journal of Biomechanics, 41: 727-736(2008).

Dalin Tang et al., 3D MRI-Based Multicomponent FSI Models for Atherosclerotic Plaques. Annals of Biomedical Engineering, 32(7): 947-960(2004).

Wang, Hongjian. IVUS-Based 2D/3D Biomechanical Model Analysis for Coronary Plaque Progression. A Dissertation Submitted to Southeast University for the Academic Degree of Master of Engineering, Jan. 3, 2017.

International Search Report for PCT/CN2017/072258 dated Oct. 18, 2017, 5 pages.

Lucian Itu et al., A Machine-learning Approach for Computation of Fractional Flow Reserve from Coronary Computed Tomography, J Appl Physiol 121: 42-52, 2016.

The Extended European Search Report in European Application No. 17731461.4 dated Jan. 3, 2019, 18 pages.

(56) References Cited

OTHER PUBLICATIONS

Jarostaw Wasilewski et al., Invasive and Non-Invasive Fractional Flow Reserve Index in Validation of Hemodynamic Severity of Intracoronary Lesions. New Methods in Diagnosis and Therapy, 2013, 9, 2(32): 160-169.

Hongjian Wang et al., Using 2D in Vivo Ivus-Based Models for Human Coronary Plaque Progression Analysis and Comparison With 3D Fsi Models. Procedia Engineering, 126(2015): 451-455.

\* cited by examiner

METHOD AND SYSTEM FOR ANALYZING BLOOD FLOW CONDITION

CROSS-REFERENCE TO RELATED APPLICATIONS

This application is a continuation of U.S. application Ser. No. 15/498,428 filed Apr. 26, 2017, which in turn is a continuation of International Application No. PCT/CN2017/072256 filed Jan. 23, 2017, the entire contents of each of which are hereby incorporated by reference.

TECHNICAL FIELD

The present disclosure generally relates to a method and system for analyzing a blood flow condition, and more particularly, to a method and system for obtaining multi-time phase blood flow parameters by employing a method of computer fluid dynamics (CFD).

BACKGROUND

CTA and MRA imaging technologies have been widely used in the diagnoses of peripheral vascular diseases, and more particularly, in the diagnoses of the vascular diseases such as vascular stenosis (vertebral artery stenosis), aneurysm, dissecting aneurysm, tumors, tumor-feeding artery, etc. The vascular analysis application provides a tool for vascular analysis in precise extraction of fine four grade blood vessels, complete bonelessness, fast automatic measurement, etc. In the analysis of blood vessels, medical image analysis systems generally employ an image segmentation technology and an image display technology for a 3-d simulation reconstruction of the blood vessels of an object. Doctors may analyze and process the lesions based on vascular morphological index (e.g., a vascular stenosis degree, a hemangioma expansion degree, etc.). However, the morphological index that may be used are not sufficient.

Computational Fluid Dynamics (CFD) is an interdisciplinary method relating to mathematics, fluid mechanics, and computer science. CFD is formed along with the development of computers since the 1950s. The main research target of CFD are simulating and analyzing fluid mechanics problems by solving control equations of fluid mechanics with computers and numerical methods. The vascular or blood flow model is an emerging application that employs computational fluid dynamics. Analyzing a single data using computational fluid mechanics cannot comprehensively reflect the actual condition and the changing rule of the analysis region. Also, selecting the time phase inaccurately may lead to a result of deviation.

SUMMARY

In one aspect of the present disclosure, a method implemented on at least one device including a processor and a storage is provided. The method may include: obtaining a first image related to a first time phase and a second image related to at a second time phase; selecting a first vascular region from the first image, wherein the first vascular region includes a blood vessel; selecting a second vascular region from the second image, wherein the second vascular region includes at least a part of the blood vessel; generating a first vascular model, wherein the first vascular model corresponds to the first vascular region; generating a second vascular model, wherein the second vascular model corresponds to the second vascular region; setting a boundary condition of the first vascular model and a boundary condition of the second vascular model; determining a condition of the blood vessel of the first vascular model at the first time phase according to the boundary condition of the first vascular model; correlating the first vascular model and the second vascular model based on the condition of the blood vessel at the first time phase; and determining a condition of the blood vessel of the second vascular model at the second time phase according to the result of correlation and the boundary condition of the second vascular model. In some embodiments, "a blood vessel" may refer to a blood vessel or a part thereof. For example, the blood vessel may include an entire coronary artery, a branch of the coronary artery, an entrance cross-section of the coronary artery, etc.

In some embodiments, the correlation of the models corresponding to different time phases may include registering the characteristic regions.

In some embodiments, the first vascular region and the second vascular region may include a coronary artery, an abdominal artery, a cerebral artery, or a lower extremity artery.

In some embodiments, the correlating the first vascular model and the second vascular model may include correlating entrances, bifurcation segments, stenosis segments, or exits of the blood vessel of the first vascular model and the second vascular model.

In some embodiments, the method may further include generating grids corresponding to the first vascular model or the second vascular model.

In some embodiments, the generating grids may include: generating 2-dimensional grids corresponding to the entrance and the exit of the first vascular model; forming grids corresponding to the side wall of the first vascular model; and generating, based on the grids corresponding to the entrance, the exit, and the side wall, 3-dimensional grids corresponding to the first vascular model.

In some embodiments, the generating grids may include: generating 2-dimensional grids corresponding to the entrance and the exit of the second vascular model; forming grids corresponding to the side wall of the second vascular model; and generating, based on the grid corresponding to the entrance, the exit, and the side wall, 3-dimensional grids corresponding to the second vascular model.

In some embodiments, the correlating the first vascular model and the second vascular model may include matching the grids corresponding to the first vascular model with the grids corresponding to the second vascular model.

In some embodiments, the condition of the blood vessel may include: blood velocity, blood pressure, wall stress of the blood vessel, wall shear stress (WSS) of the blood vessel, or fractional flow reserve (FFR).

In some embodiments, the boundary condition of the first vascular model may include: determining that the first vascular model is abnormal; in response to the determination that the first vascular model is abnormal, determining an abnormal region; generating a normal model corresponding to the first vascular model; obtaining a boundary condition of the normal model; and generating, based on the boundary condition of the normal model, a boundary condition corresponding to the first vascular model.

In some embodiments, the abnormal vascular model may include vascular stenosis, vascular hypertrophy, or angioma.

In some embodiments, the method may further include generating a relationship between a condition of the blood vessel and a time phase, based on the condition of the blood vessel of the first vascular model at the first time phase and the condition of the blood vessel of the second vascular model at the second time phase.

In some embodiments, the method may further include determining, based on the relationship between the condition of the blood vessel and time, a condition of the blood vessel at a third time phase.

In some embodiments, the determining the condition of the blood vessel of the first vascular model at the first time phase, or the determining a condition of the blood vessel of the second vascular model at the second time phase, comprises employing a method of computational fluid dynamics (CFD).

In one aspect of the present disclosure, a system including at least one processor and a storage device is provided. The system may include a receiving module. The receiving module may be configured to obtain a first image at a first time phase and a second image of at a second time phase. The system may further include a multi-time phase feature generation module. The multi-time phase feature generation module may be configured to: select a first vascular region from the first image, wherein the first vascular region includes a blood vessel; select a second vascular region from the second image, wherein the second vascular region includes at least a part of the blood vessel; generate a first vascular model, wherein the first vascular model corresponds to the first vascular region; generate a second vascular model, wherein the second vascular model correspond to the second vascular region; set a boundary condition of the first vascular model and a boundary condition of the second vascular model; determine a condition of the blood vessel of the first vascular model at the first time phase, according to the boundary condition of the first vascular model; correlate the first vascular model and the second vascular model, based on the condition of the blood vessel at the first time phase; determine a condition of the blood vessel of the second vascular model at the second time phase, according to the result of correlation and the boundary condition of the second vascular model.

In one aspect of the present disclosure, a method implemented on at least one device including a processor and a storage is provided. The method may include: obtaining a 2-dimensional image, wherein the 2-dimensional image includes one or more regions of interest; extracting a plurality of boundary points of the one or more regions of interest; determining a first region and a second region, according to the boundary points; generating, based on a first grid division control condition, grids of the first region; generating, based on a second grid division control condition, grids of the second region, wherein the second grid division control condition differs from the first grid division control condition; and analyzing, according to the grids of the first region and the grids of the second grid, the one or more regions of interest.

In some embodiments, the one or more regions of interest may include at least one of a coronary artery, an abdominal artery, a cerebral artery, or a lower extremity artery.

In some embodiments, the grids of the first region or the grids of the second region are generated based on Delaunay triangulation (DT).

In some embodiments, the first grid division control condition may include a first area constraint condition.

In some embodiments, the first area constraint condition may include limiting the area of all grids to be smaller than or equal to an area constraint value.

In some embodiments, the second grid division control condition may include a second area constraint condition that differs from the first area constraint condition.

In some embodiments, the method may further include determining, according to the plurality of boundary points, a third region, wherein the third region is not divided into grids.

In some embodiments, the analyzing the region of interest (ROI) comprises analyzing a dynamic parameter of the region of interest, by employing a method of computational fluid dynamics (CFD). The dynamic parameter may include blood velocity, blood pressure, wall stress of the blood vessel, wall shear stress (WSS) of the blood vessel, fractional flow reserve (FFR), or value of coronary flow reserve (CFR).

In some embodiments, the method may further include: obtaining a 3-dimensional image, wherein the 3-dimensional image may include the one or more regions of interest; and generating 3-dimensional grids corresponding to the 3-dimensional image based on the grids of the first region and the grids of the second region.

In another aspect of the present disclosure, a system including at least one processor and a storage device is provided. The system may include a receiving module. The receiving module may be configured to: obtain a 2-dimensional image, wherein the 2-dimensional image may include one or more regions of interest. The system may further include a multi-time phase feature generation module. The multi-time phase feature generation module may be configured to: extract a plurality of boundary points of the one or more regions of interest; determine, according to the plurality of boundary points, a first region and a second region; generate, based on a first grid division control condition, grids of the first region; generate, based on a second grid division control condition, grids of the second region, wherein the second grid division control condition differs from the first grid division control condition; and analyzing, according to the grids of the first region and the grids of the second region, the one or more regions of interest.

In another aspect of the present disclosure, a method to be implemented on at least one device including a processor and a storage is provided. The method may include: obtaining vascular images of multiple time phases, including a first vascular image at a first time phase and a second vascular image of at a second time phase, wherein the vascular images of multiple time phases correspond to a same blood vessel or a part thereof; generating multiple vascular models, wherein the multiple vascular models correspond to the vascular images of multiple time phases; obtaining multiple conditions, including a first vascular condition and a second vascular condition, of the blood vessel or the part thereof according to the multiple vascular models, wherein the first vascular condition corresponds to the first vascular image, and the second vascular condition corresponds to the second vascular image; obtaining a relationship between the condition of the blood vessel or the part thereof and time, according to the multiple conditions of the blood vessel or the part thereof; and obtaining a third vascular condition of the blood vessel or the part thereof, according to the relationship. Herein, a "vascular image" corresponding to a "blood vessel" may refer to that the vascular image including an image of the blood vessel. For example, a blood vessel may include an aortic or a part thereof, a coronary or a part thereof, etc.

In some embodiments, the blood vessel may include at least one of a coronary artery, an abdominal artery, a cerebral artery, or a lower extremity artery.

In some embodiments, the third vascular condition may be an average fractional flow reserve (FFR).

In some embodiments, the method may further include: correlating the multiple vascular models; and analyzing, according to the result of correlation, the multiple conditions of blood vessels employing a method of computational fluid dynamics (CFD).

In some embodiments, the correlating the multiple vascular models may include correlating at least two of the vascular models at entrances, bifurcation segments, stenosis segments, or exits of the blood vessel.

In some embodiments, the method may further include generating grids of the multiple vascular models.

In some embodiments, the method may further include matching the grids of the multiple vascular model.

In another aspect of the present disclosure, a system including at least one processor and a storage device is provided. The system may include a receiving module. The receiving module may be configured to: obtain vascular images at multiple time phases, including a first vascular image at a first time phase and a second vascular image at a second time phase, wherein the vascular images at multiple time phases may correspond to a same blood vessel or a part thereof respectively. The system may further include a multi-time phase feature generation module. The multi-time phase feature generation module may be configured to: generate multiple vascular models, wherein the multiple vascular models may correspond to the vascular images at multiple time phases; obtain multiple conditions, including a first vascular condition and a second vascular condition, of the blood vessel or the part thereof, according to the multiple vascular models, wherein the first vascular condition may correspond to the first vascular image, and the second vascular condition may correspond to the second vascular image; obtain a relationship between the condition of the blood vessel or the part thereof and time, according to the multiple conditions of the blood vessel or the part thereof; and obtain a third vascular condition of the blood vessel or the part thereof, according to the relationship.

In another aspect of the present disclosure, a method implemented on at least one device including a processor and a storage is provided. The method may include: obtain a first vascular model, wherein the first vascular model may correspond to a blood vessel including a first region; obtain one or more parameters of the first vascular model; determine, according to the one or more parameters of the first vascular model, a position of the first region of the first vascular model; generate a second vascular model including the blood vessel or a part thereof, wherein the first region of the blood vessel of the second vascular model may be modified compared to the first region of the blood vessel of the first vascular model; obtain a boundary condition of the second vascular model; determine, according to the boundary condition of the second vascular model, a parameter of the second vascular model; determine, according to the parameter of the second vascular model, a boundary conditions of the first vascular model; and obtain, according to the boundary condition of the first vascular model, a blood flow condition of the first vascular model.

In some embodiments, the first region may include a region of vascular stenosis, vascular hypertrophy, or angioma.

In some embodiments, the one or more parameters of the first vascular model may include a cross-sectional area of the blood vessel.

In some embodiments, the modifying the first region of the first vascular model may include dilating or narrowing the blood vessel.

In some embodiments, the boundary condition of the second vascular model may include blood pressure, blood velocity, blood viscosity, pressure, or wall stress, of an entrance, an exit, or a side wall of the blood vessel of the second vascular model.

In some embodiments, the parameter of the second vascular model may include flow resistance, blood velocity, blood pressure, wall stress of the blood vessel, wall shear stress (WSS) of the blood vessel, or fractional flow reserve (FFR).

In some embodiments, the determining a parameter of the second vascular model may include performing a computational fluid dynamics (CFD) analysis.

In some embodiments, the method may further include determining a dynamic parameter of the first vascular model according to the boundary condition of the first vascular model.

In another aspect of the present disclosure, a system including at least a processer and a storage device is provided. The system may include a receiving nodule. The receiving module may be configured to obtain a first vascular model, wherein the first vascular model may include a first region; obtain one or more parameters of the first vascular model. The method may further include a multi-time phase feature generation module. The multi-time phase feature generation module may be configured to: determine, according to the one or more parameters of the first vascular model, a position of the first region of the first vascular model; generate a second vascular model by modifying the first region of the first vascular model; obtain a boundary condition of the second vascular model; determine, according to the boundary conditions of the second vascular model, a parameter of the second vascular model; determine, according to the parameter of the second vascular model, a boundary condition of the first vascular model; and obtain, according to the boundary condition of the first vascular model, a blood flow condition of the first vascular model.

Some of appended features of the present disclosure are illustrated in the following description. The appended features of the present disclosure are obvious to those skilled in the art, under the teaching of the description with appended drawings or the productions/operations of the embodiments. The features of the present disclosure may be implemented and realized by the practice or use of various methods, means and combinations of various aspects of the embodiments described below.

BRIEF DESCRIPTION OF THE DRAWINGS

The present disclosure is further described in terms of schematic embodiments. These schematic embodiments are described in detail with reference to the drawings. The drawings are not to scale. These embodiments are non-limiting schematic embodiments, in which like reference numerals represent similar structures throughout the several views of the drawings, and wherein.

DETAILED DESCRIPTION

Figure 1A:
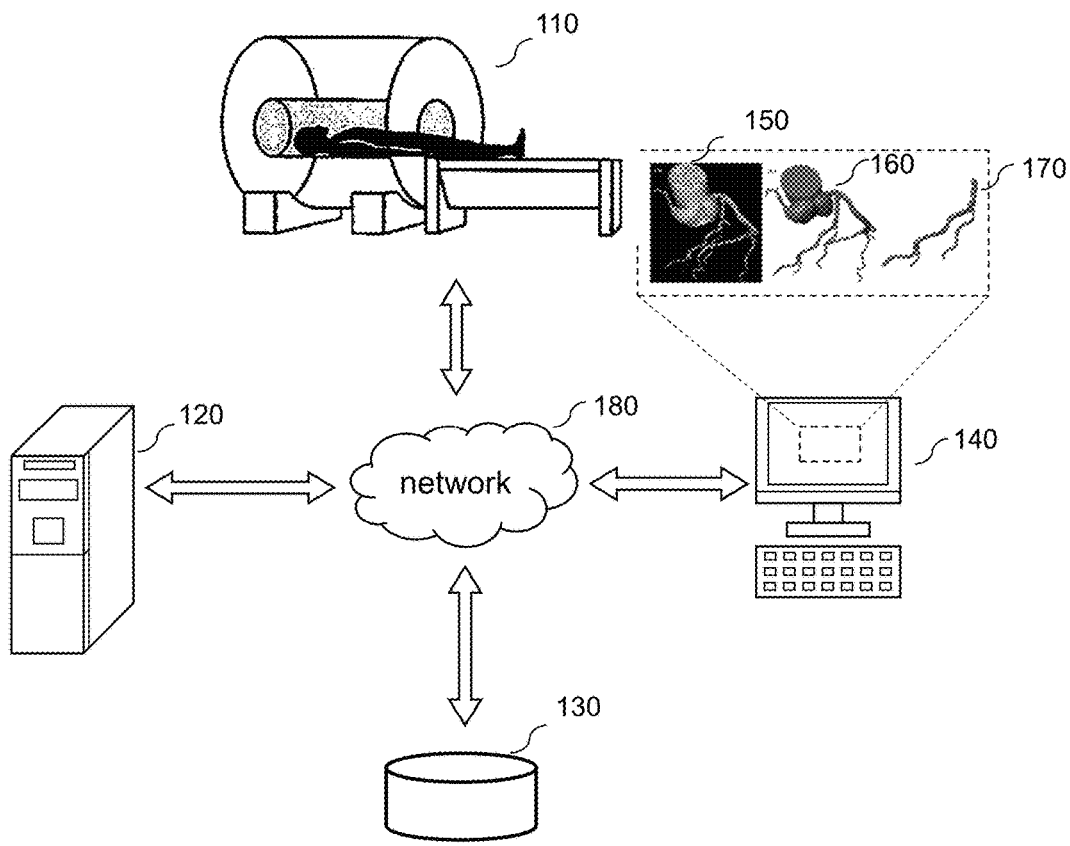
FIG. 1A illustrates a schematic diagram of a blood flow condition analysis system according to some embodiments of the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As used in the disclosure and the appended claims, the singular forms "a," "an," and "the" include plural referents unless the content clearly dictates otherwise. It will be further understood that the terms "comprises," "comprising," "includes," and/or "including" if used in the disclosure, specify the presence of stated steps and elements, but do not preclude the presence or addition of one or more other steps and elements.

Some modules of the system may be referred to in various ways according to some embodiments of the present disclosure, however, any amount of different modules may be used and operated in a client terminal and/or a server. These modules are intended to be illustrative, not intended to limit the scope of the present disclosure. Different modules may be used in different aspects of the system and method.

According to some embodiments of the present disclosure, flow charts are used to illustrate the operations performed by a data processing system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

In the process of image processing, "image segmentation", "image extraction", and "image classification" may each means selecting an image that satisfies a specific condition from a large region and may be used interchangeably. According to some embodiments of the present disclosure, an imaging system may include one or more formats. The formats may include but are not limited to digital subtraction angiography (DSA), magnetic resonance imaging (MRI), magnetic resonance angiography (MRA), computed tomography (CT), computed tomography angiography (CTA), ultrasonic scanning (US), positron emission tomography (PET), single photon mission computed tomography (SPECT), SPECT-MR, CT-PET, CE-SPECT, DSA-MR, PET-MR, PET-US, SPECT-US, TMS-MR, US-CT, US-MR, X-ray-CT, X-ray-PET, X-ray-US, video-CT, video-US, or the like, or any combination thereof. In some embodiments, a subject of image scanning may include an organ, a body, an object, an injured section, a tumor, or the like, or any combination thereof. In some embodiments, a subject of image scanning may include a brain, a thorax, an abdomen, an organ, a bone, a vessel, or the like, or any combination thereof. In some embodiments, a subject of image scanning may include blood vessels of one or more tissues. In some embodiments, the image may include a 2-dimensional image and/or a 3-dimensional image. A smallest divisible element of the 2-dimensional image may be a pixel. A smallest divisible element of the 3-dimensional image may be a voxel. The 3-dimensional image may include a series of 2-dimensional slices and/or 2-dimensional layers.

A process of image segmentation may be performed based on features corresponding to the pixels (or voxels) of an image. In some embodiments, the features corresponding to the pixels (or voxels) may include texture, grayscale, average grayscale, signal strength, color saturation, contrast, brightness, or the like, or any combination thereof. In some embodiments, a spatial position feature corresponding to the pixels (or voxels) may be used in the process of image segmentation.

The present disclosure relates to a method and system for obtaining blood flow conditions. In a process of determining blood flow conditions, images of multiple time phases may be obtained, and multiple vascular models corresponding to multiple time phases may be generated. The multiple vascular models may be correlated to obtain boundary conditions of the multiple vascular models. According to the boundary conditions, condition of blood vessel of the multiple vascular models may be determined.

FIG. 1A illustrates a schematic diagram of a blood flow condition analysis system 100 according to some embodiments of the present disclosure. The blood flow condition analysis system 100 may include a data collection device 110, a processing device 120, a storage device 130, and a communication device 140. The data collection device 110, the processing device 120, the storage device 130, and the communication device 140 may communicate with each other via a network 180.

The data collecting device 110 may be configured to collect data. The data may include image data, object's features, etc. In some embodiments, the data collecting device 110 may include an imaging device. The imaging device may collect the image data. The imaging device may be a magnetic resonance imaging (MRI) device, a computed tomography (CT) device, a positron emission computed tomography (PET) device, a b-scan ultrasonography device, an ultrasonic diagnostic device, a thermal texture mapping (TTM) device, a medical electronic endoscope (MEE) device, or the like, or any combination thereof. The image data may include images or data of a blood vessel, a tissue, or an organ of an object. In some embodiments, the data collection device may include an object feature collection device. The object feature collection device may collect object features such as heart rate, heart rhythm, blood pressure, blood velocity, blood viscosity, cardiac output, myocardial mass, vascular flow resistance, and/or other object features associated with blood vessels, tissues or organs. In some embodiments, the object feature collection device may obtain age, height, weight, gender, or other features of the object. In some embodiments, the image data and the object features may be multi-time phase data. For example, the multi-time phase data may include data obtained from a same or similar position of an object at different time points or time phases. In some embodiments, the object feature collection device may be integrated in the imaging device so that the image data and the object's features may be collected simultaneously. In some embodiments, the data collection device 110 may send the collected data to the processing device 120, the storage device 130, and/or the communication device 140 via the network 180.

The processing device 120 may process data. The data may be collected by the data collection device 110. The data may also be obtained from the storage device 130, the communication device 140 (e.g., input data of a user), or from a cloud or an external device via the network 180. In some embodiments, the data may include image data, object's features data, user input, etc. The processing of the data may include selecting a region of interest from the image data. The region of interest may be selected solely by the processing device 120, or selected based on user input. In some embodiments, the region of interest may include a blood vessel, a tissue, an organ, etc. For example, the region of interest may be an artery, such as a coronary artery, an abdominal artery, a brain artery, a lower extremity artery, etc. The processing device 120 may further segment the region of interest. The technique of image segmentation may include a technique based on edges (e.g., a Perwitt operator, a Sobel operator, a gradient operator, a Kirch operator, etc.), a technique based on regions (e.g., a region growing technique, a threshold technique, a clustering technique, etc.), or other techniques based on fuzzy sets, a neural network, etc.

The processing device 120 may reconstruct a model that corresponds to the region of interest. The model may be selected based on the object's features, features of the region of interest, etc. For example, if selecting the coronary artery as the region of interest, the processing device 120 may segment an image that includes a coronary artery to extract an image of the coronary artery. The processing 120 may reconstruct the model according to the object features, general features of the coronary artery, image features of the coronary artery, etc. The reconstructed model may correspond to a vascular shape or a blood flow shape of the coronary artery. After reconstructing the model of the region of interest, the processing device 120 may preform analysis and computation based on the model. Techniques of analysis and computation may include computed fluid dynamics, etc.

In some embodiments, the processing device 120 may obtain data at multiple time phases. For example, the processing device 120 may obtain images of the coronary artery of an object at five different time phases. In such situation, the processing device 120 may reconstruct models corresponding to regions of interest (e.g., an entire coronary artery, a branch of the coronary artery, a cross section of a blood entrance of the coronary artery, etc.) at different time phases respectively. The processing device 120 may then analyze and compute the models in sequence. In some embodiments, the processing device 120 may generate grids or meshes (also referred to as grid process or grid division) on the models at different time phases. The processing device 120 may correlate the grid processed models with each other to reduce computation load and improve computational accuracy. Techniques of correlating and grid processing may be found elsewhere in the present disclosure, for example, in FIG. 6, FIG. 11 and their corresponding descriptions. In some embodiments, the analysis and computation result may include a physical state and a coefficient/parameter of a blood vessel, a tissue, or an organ. For example, a result of analysis and computation of the model of coronary artery may include a hemodynamic parameter such as blood velocity, blood pressure, wall stress of the blood vessel, wall shear stress (WSS) of the blood vessel, fractional flow reserve (FFR), coronary flow reserve (CFR), or the like, or any combination thereof. In some embodiments, the processing device 120 may generate a relationship between the physical state and/or the coefficient/parameter and time phase (e.g., changes of hemodynamic parameter with time). In some embodiments, the relationship may be generated based on the results of analysis and computation at different time phases. The relationship may be represented by a curve or a table. The processing device 120 may obtain physical states and/or coefficients/parameters of the regions of interest at any time phase based on the curve or the table.

In some embodiments, the processing device 120 may denoise or smooth obtained data or a processing result. In some embodiments, the processing device 120 may send the obtained data or the processing result to the storage device 130 for storing, or the communication device 140 for displaying. The processing result may be an intermediate result generated in the process (e.g., a model of a region of interest), or a final result of the process (e.g., an analyzed and computed hemodynamic parameter, etc.). In some embodiments, the processing device 120 may be one or more processing units or devices, such as central processing units (CPUs), graphics processing units (GPUs), digital signal processors (DSPs), systems on a chip (SoC), microcontroller units (MCUs), etc. In some embodiments, the processing device 120 may be a specially designed processing unit or device with specific functions. The processing device 120 may be local, or remote with respect to the data collection device 110.

The storage device 130 may store data or information. The data or information may include data obtained by the data collection device 110, processing results or control instructions generated by the processing device 120, user input received by the communication device 140, etc. The storage device 130 may be one or more storage mediums with read/write functions. The storage device 130 may include but not limited to a static random access memory (SRAM, a random-access memory (RAM), a read-only memory (ROM), a hard disk, a flash memory, etc. In some embodiments, the storage device 130 may be a remote storage device, such as a cloud disk, etc.

The interactive 140 may be configured to receive, send, and/or display data or information. The received data or information may include the data obtained by the data collection device 110, the processing results generated by the processing device 120, the data stored by the storage device 130, etc. For example, the data or information displayed by the communication device 140 may include an actual image 150 of a cardiovascular obtained by the data collection device 110, a cardiovascular model 160 reconstructed by the processing device 120 based on the actual image 150, a coronary artery model extracted from the cardiovascular model 160 by the processing device 120, etc. The formats of display may include but is not limited to a 2-dimensional or 3-dimensional medical image, a geometric model and its grid processed result, a vector diagram (e.g., a velocity vector), a contour map, a filled contour map (cloud chart), an XY scatter plot, a particle trajectory map, a simulated flow effect, or the like, or any combination thereof. As another example, the data or information sent by the communication device 140 may include input information of a user. The communication device 140 may receive one or more operating parameters of the processing device 120 input by the user, and send the operating parameters to the processing device 120.

In some embodiments, the communication device 140 may include a user interface. The user may provide a user input to the communication device 140 by specific interactive apparatuses such as a mouse, a keyboard, a touchpad, a microphone, etc. For example, the user may click on the model displayed by the communication device 140 and select a region of interest of the model. As another example, the user may select any position of the vascular model displayed by the communication device 140. The communication device 140 may then obtain a blood velocity, a blood pressure, a blood flow, etc. of that position from the processing device 120 and display them.

In some embodiments, the communication device 140 may be a device with displaying function, such as a screen. In some embodiments, the communication device 140 may have some or all functions of the processing device 120. For example, the communication device 140 may implement operations (e.g., smoothing, denoising, changing colors, etc.) to the results generated by the processing device 120. Merely by way of example, the operation of changing colors may include transferring a grayscale image to a color image, or transferring a color image to a grayscale image. In some embodiments, the communication device 140 and the processing device 120 may be an integrated device. The integrated device may implement functions of both the processing device 120 and the communication device 140. In some embodiments, the communication device 140 may include a desktop computer, a server, a mobile device, etc. The mobile device may include a laptop computer, a tablet computer, an iPad, a built-in device of a vehicle (e.g., a motor vehicle, a ship, an airplane), a wearable device, etc. In some embodiments, the communication device 140 may include or is connected to a display apparatus, a printer, a fax machine, etc.

The network 180 may be used for internal communication of thein blood flow condition analysis system 100. The network 180 may also be configured to receive information from or send information to the external devices outside the system 100. In some embodiments, the data collection device 110, the processing device 120, and the communication device 140 may be connected to the network 180 via a wired connection, a wireless connection, or a combination thereof. The network 180 may be a single network or a combination of networks. In some embodiments, the network 180 may include but is not limited to a local area network (LAN), a wide area network (WAN), a public network, a proprietary network, a wireless local area network (WLAN), a virtual network, an urban metropolitan area network, a public switched telephone network (PSTN), or the like, or any combination thereof. In some embodiments, the network 180 may include multiple network access points, such as a wired or wireless access point, a base station or network switched point, etc. Through these access points, any data source may be connected to the network 180 and transmit information via the network 180.

Figure 1B:
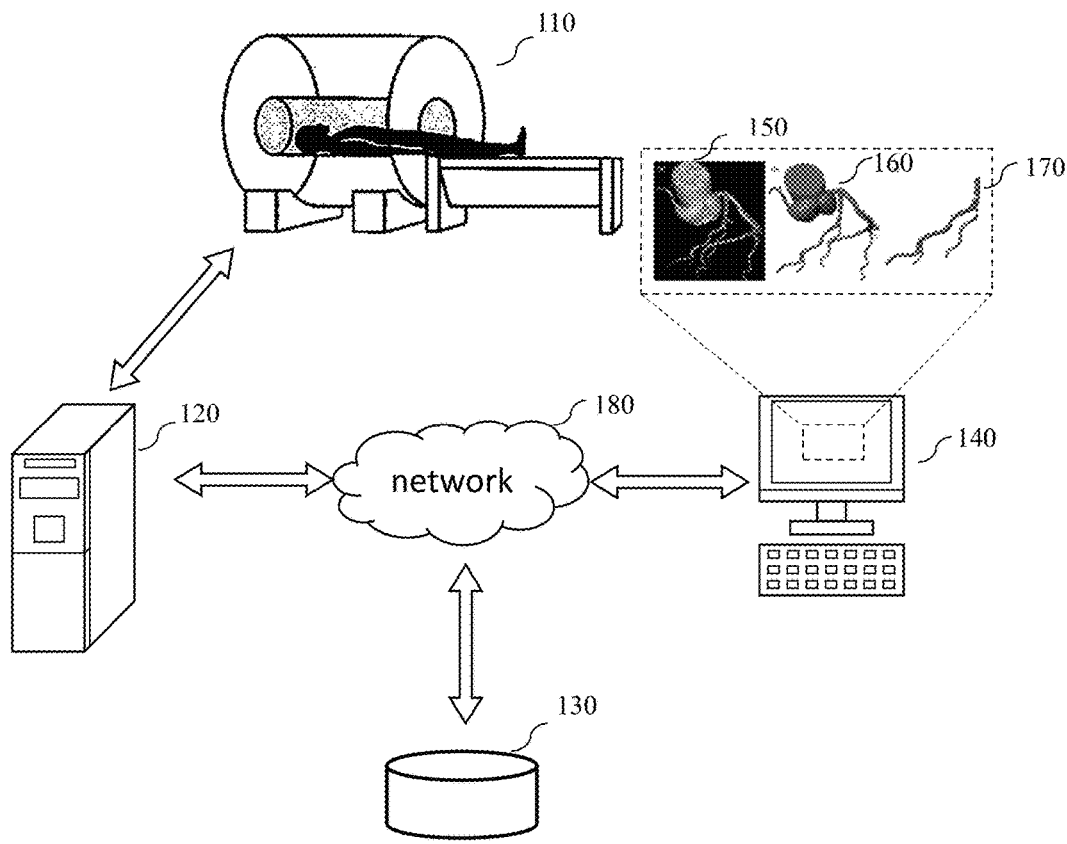
FIG. 1B illustrates another schematic diagram of a blood flow condition analysis system according to some embodiments of the present disclosure.

FIG. 1B illustrates another schematic diagram of a network environment including a blood flow condition analysis system 100 according to some embodiments of the present disclosure. FIG. 1B is similar to FIG. 1A. In FIG. 1B, the processing device 120 may be directly connected to the data connection device 110. The data connection device 110 may not directly connect to the network 180.

The above description of the present disclosure is provided for the purposes of illustration, and not intended to limit the scope of the present disclosure. For persons having ordinary skills in the art, modules may be combined in various ways, or connected with other modules as subsystems. Various variations and modifications may be conducted under the teaching of the present disclosure. However, those variations and modifications may not depart the spirit and scope of this disclosure. For example, the data connection device 110, the processing device 120, and the communication device 140 may directly exchange information with each other without the network 180. As another example, the devices may exchange information by a removable storage device or another intermediate medium.

Figure 2:
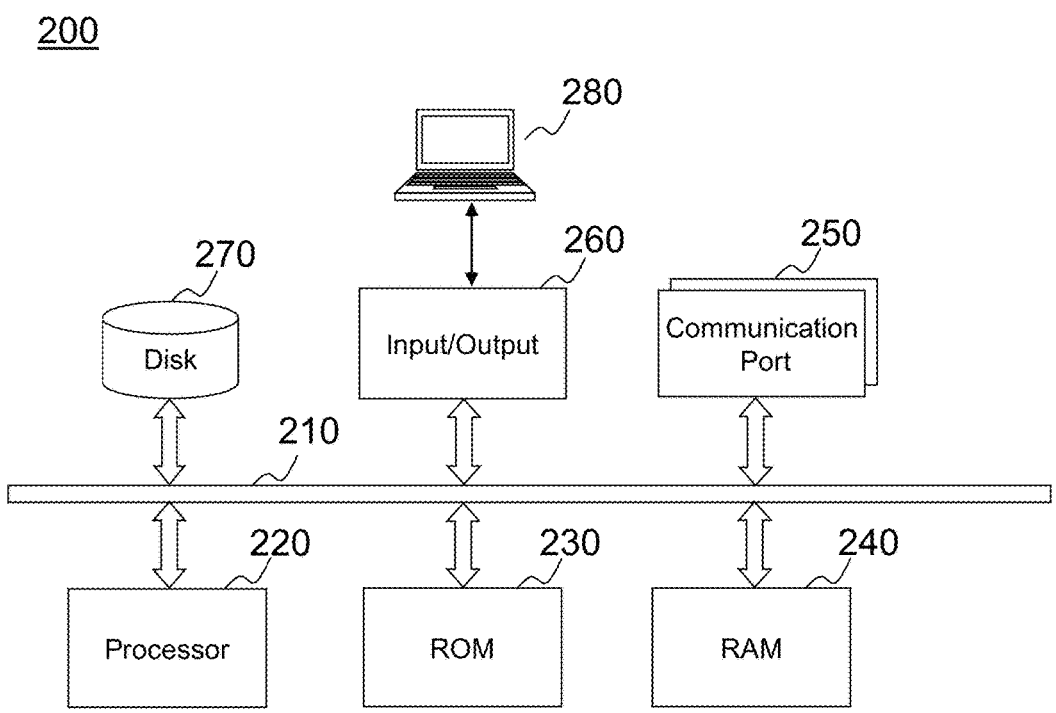
FIG. 2 illustrates a structure of a computing device that can implement a specific system according to some embodiments of the present disclosure.

FIG. 2 illustrates a structure of a computing device 200 that can implement a specific system according to some embodiments of the present disclosure. The computing device 200 may implement a specific system of the present disclosure. The specific system of the present disclosure may use a functional diagram to describe a hardware platform including a user interface. The computing device 200 may configured to implement one or more components, modules, units, sub-units (e.g., the processing device, the interactive device, etc.) of the blood flow condition analysis system 100. The one or more components, modules, units, sub-units (e.g., the processing device, the interactive device, etc.) of the blood flow condition analysis system 100 may be implemented by the computing device 200 by a hardware device, a software program, a firmware, or any combination thereof of the computing device 200. The computing device 200 may be a general purpose computing device, or a specific purpose computing device. The computing devices may be configured to implement the specific system of the present disclosure. For brevity, the FIG. 2 illustrates only one computing device. According to some embodiments, functions of processing and pushing information may be processing loads of a decentralized system implemented on a set of similar platforms in a distributed manner.

As showed in FIG. 2, the computing device 200 may include an internal communication bus 210, a processor 220, a read-only memory (ROM) 240, a random-access memory (RAM) 240, a communication port 250, an input/output component 260, a hard disk 270, a user interface 280, etc. The internal communication bus 210 may be configured to implement data communications between components of the computing device 200. The processor 220 may implement program instructions to complete one or more functions, components, modules, units, sub-units of the blood flow condition analysis system 100 disclosure in the present disclosure. The processor 220 may include one or more processors. The commination port 250 may be configured to implement data communications (e.g., via the network 180) between the computing device 200 and other parts (e.g., the data connection device 110) of the blood flow condition analysis system 100. The computing device 200 may include different forms of program storage unit and data storage unit, such as a hard disk 270, a read-only memory (ROM) 230, a random access memory (RAM) 240, various data files used by a computing device for processing or communication, a possible program instruction implemented by the processor 220. The input/output component 260 may support inputting/outputting data stream between the computing device 200 and other components (e.g., the user interface 280), and/or other components of the blood flow condition analysis system 100. The computing device 200 may send and receive information and data by the communication port 250 via the network 180.

Figure 3:
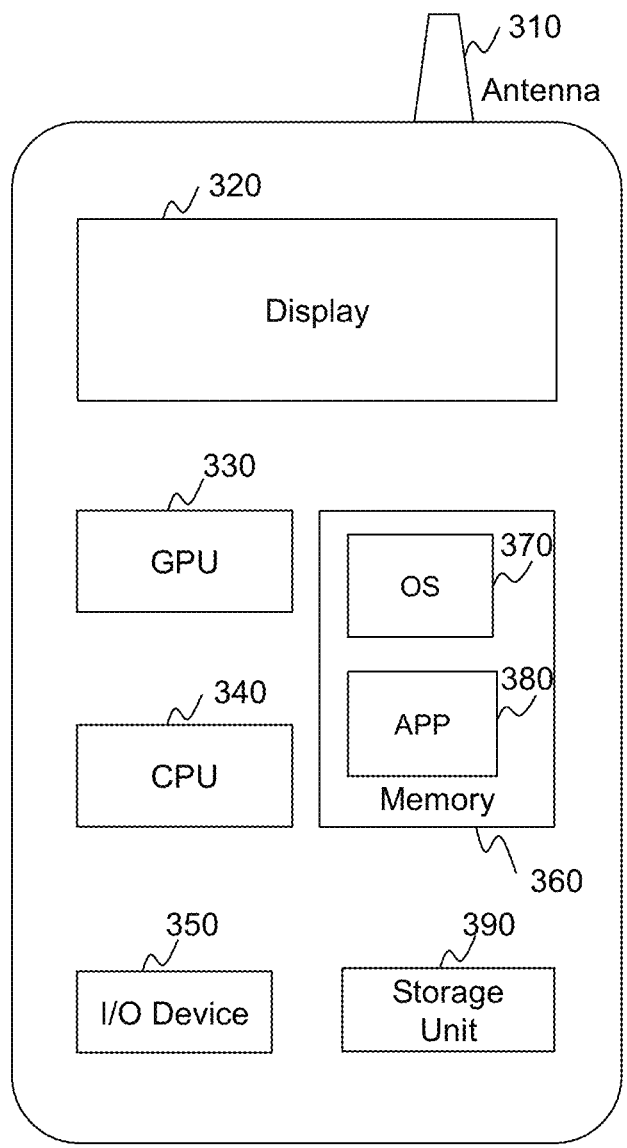
FIG. 3 illustrates a schematic diagram of a mobile device that can implement a specific system according to some embodiments of the present disclosure.

FIG. 3 illustrates a schematic diagram of a mobile device that can implement a specific system according to some embodiments of the present disclosure. In some embodiments, a user device that is configured to display information related to an interactive position may be a mobile device 300. The mobile device 300 may include a smart phone, a tablet computer, a music player, a portable game console, a GPS receiver, a wearable calculating device (e.g. glasses, watches, etc.), etc. The mobile device 300 may include one or more central processing units (CPUs) 340, one or more graphical processing units (GPUs) 330, a display 320, a memory 360, an antenna 310 (e.g. a wireless communication unit), a storage unit 390, and one or more input/output (I/O) devices 350. Moreover, the mobile device 300 may also include any other suitable component that includes but is not limited to a system bus or a controller (not shown in FIG. 3). As shown in FIG. 3, a mobile operating system 370 (e.g. iOS, Android, Windows Phone, etc.) and one or more applications 380 may be loaded from the storage unit 390 to the memory 360 and implemented by the CPUs 340. The application 380 may include a browser or other mobile applications configured to receive and process information related to the images or blood flow condition analyses in the mobile device 300. The communication information related to the images or blood flow condition analyses between the user and the one or more components of the system 100 may be obtained through the I/O device 350, and provide the information to the processing device 120 and/or other modules or units of the system 100, e.g. the network 180.

Figure 4A:
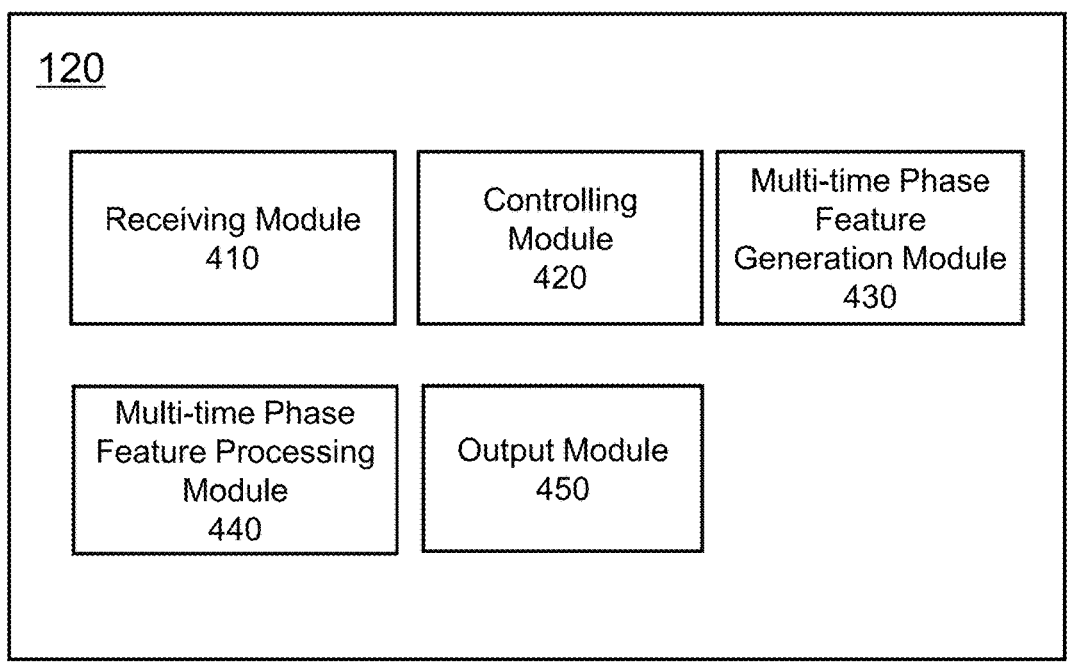
FIG. 4A illustrates a schematic diagram of an exemplary processing device according to some embodiments of the present disclosure.

FIG. 4A illustrates a schematic diagram of an exemplary processing device according to some embodiments of the present disclosure. The processing device 120 may include a receiving module 410, a controlling module 420, a multi-time phase feature processing module 440, and an output module 450.

The receiving module 410 may obtain image data, object's features, etc. from the data collection device 110 and/or the storage device 130. The image data may include an image or data of a blood vessel, a tissue, or an organ of an object. The object's features may include heart rate, heart rhythm, blood pressure, blood velocity, blood viscosity, cardiac output, myocardial mass, vascular flow resistance, and other object's features related to the blood vessel, the issue or the organ. The object's features may also include age, height, weight, gender, or other features of the object. In some embodiments, the image data and the object's features may be multi-time phase data. For example, the multi-time phase data may include data obtained from a same or similar position of the object at different time points or time phases.

The controlling module 420 may generate a control instruction. The control instruction may instruct another module to implement an operation such as inputting, outputting, storing, processing, etc. For example, the control instruction may instruct the receiving module 410 to receive needed data. As another example, the instruction may instruct the multi-time phase feature generation module 430 to generate a multi-time phase feature.

The multi-time phase feature generation module 430 may be configured to generate a multi-time phase feature. The multi-time phase feature may include a multi-time phase model, a multi-time phase parameter, a multi-time phase boundary condition, a multi-time phase analysis result, etc. More particularly, for example, the multi-time phase generation module 430 may select regions of interest from the multi-time phase image data. The region of interest may be selected solely by multi-time phase feature generation module 430, or selected based on user input. In some embodiments, the region of interest may be a blood vessel, a tissue, an organ, etc. For example, the region of interest may include an artery(s), such as a coronary artery, an abdominal artery, a brain artery, a lower extremity artery, etc. The regions of interest selected from the multi-time phase image may correspond to the region of interest. For example, the region of interest may include at least parts of a same blood vessel, a tissue, an organ, etc., as the region of interest. The multi-time phase generation module 430 may further segment the region of interest. The technique of image segmentation may include a technique based on edges (e.g., a Perwitt operator, a Sobel operator, a gradient operator, a Kirch operator, etc.), a technique based on regions (e.g., a region growing technique, a threshold technique, clustering technique, etc.), or other techniques based on fuzzy sets, a neural network, etc. In some embodiments, the multi-time phase generation module 430 may segment the regions of interest of the multi-time phase image simultaneously. In some embodiments, the multi-time phase generation module 430 may segment the regions of interest of the multi-time phase image in sequence.

The multi-time phase generation module 430 may reconstruct a model of the region of interest to generate a multi-time phase model. The model may be selected based on the object's features, features of the region of interest, etc. For example, if coronary artery is selected as the region of interest, the multi-time phase generation module 430 may segment an image that includes a coronary artery to extract an image of the coronary artery. Then the multi-time phase generation module 430 may reconstruct the model according to the object features, general features of the coronary artery, image features of the coronary artery, etc. The reconstructed model may correspond to a vascular shape or a blood flow shape of the coronary artery. After reconstructing the model of the region of interest, the multi-time phase generation module 430 may set parameters and boundary conditions, and may implement analysis and computation based on the model. The technique of setting the parameters and the boundary conditions may be found elsewhere in the present disclosure.

The multi-time phase processing module 440 may process a generated multi-time phase computing result (also referred to as post-processing). The processing may include generate a curve or table of a relationship between the computation result of the model and time phase using curve-fitting, interpolation, etc. According to the curve or table of the relationship, the multi-time phase processing module 440 may further generate an estimated value of the analysis result at any time phase. The steps and results of the post-processing may be found in FIG. 13 and its corresponding descriptions. In some embodiments, the multi-time phase processing module 440 may compare the generated multi-time phase computation result (e.g., a vascular condition) and a reference result to generate a comparison result. The reference result may be stored in the storage device 130 or the network 180, or input by a user. In some embodiments, the reference result and the related comparison result may be stored in a table. For example, if the computation result is the blood velocity, the reference result may be a relationship between a range of the blood velocities and their corresponding degree of risk. The degree of risk may be divided into normal, warning, dangerous, extremely dangerous, etc. In some embodiments, the user may input the relationship manually based on clinical experiences. In some embodiments, the comparison may be a comparison of computation results of a same object at different time periods.

The output module 450 may output the generated multi-time phase computation result or data. For example, the output module 450 may send the multi-time phase result or features to the storage device 130 for storing, or to the communication device 140 for displaying. In some embodiments, the multi-time phase feature processing module 440 or the output module 450 may denoise or smooth the multi-time phase feature or the computation result before outputting. The multi-time phase computation result may be a generated intermediate result (e.g., a model of a region of interest), or a generated final result (e.g., an analyzed and computed hemodynamic parameter, a curve or table of a relationship between the computation result and time phase, etc.).

Figure 4B:
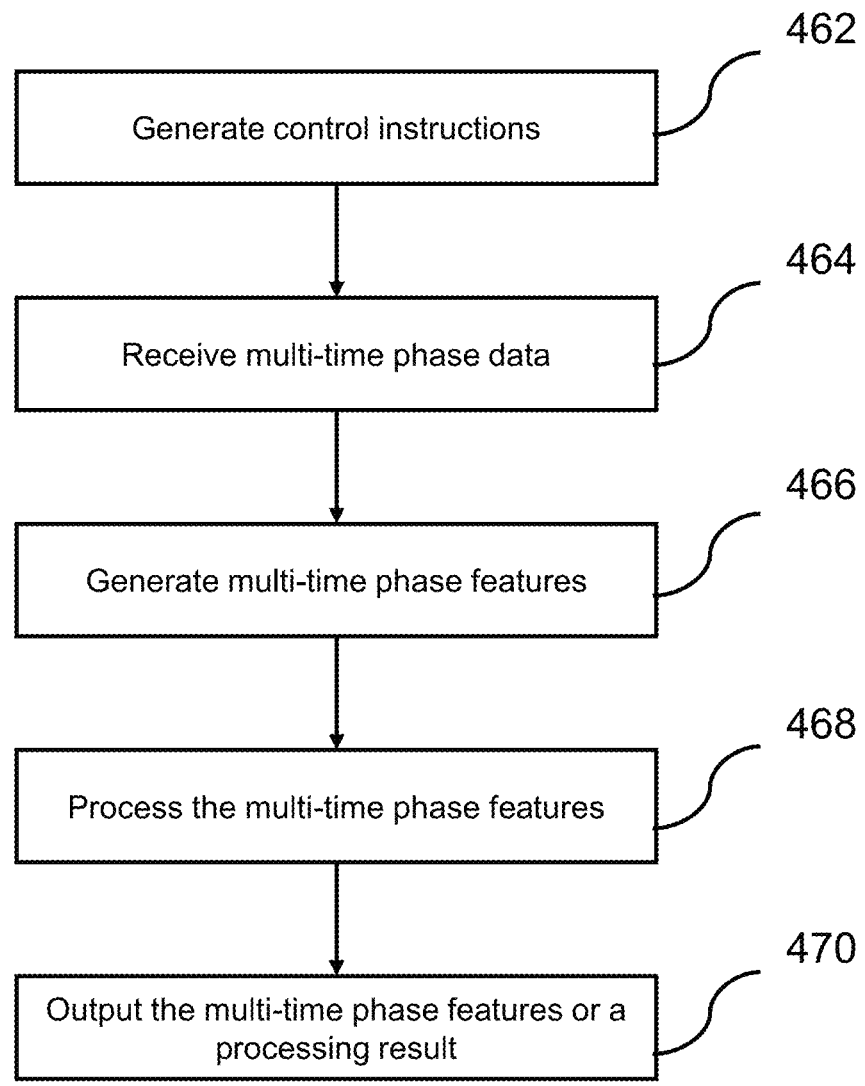
FIG. 4B is a flow chart illustrating a process for processing multi-time phase features according to some embodiments of the present disclosure.

FIG. 4B is a flow chart illustrating a process for processing multi-time phase features according to some embodiments of the present disclosure. In some embodiments, the process 400 may be implemented by the processing module 120.

In 462, one or more control instructions may be generated. In some embodiments, 462 may be implemented by the controlling module 420. The control instructions may instruct implementation of other steps in the process 400.

In 464, multi-time phase data may be received. In some embodiments, 464 may be implemented by the receiving module 410. The multi-time phase data may include multi-time phase image data and multi-time phase object's features. In some embodiments, the multi-time phase object's features may be continuous object's features or features curves on time.

In 466, multi-time phase feature may be generated. In some embodiments, 466 may be implemented by the multi-time phase feature generation module 430. The multi-time phase feature may include a multi-time phase model, a multi-time phase parameter, a multi-time phase boundary condition, a multi-time phase analysis result, etc.

In 468, the generated multi-time phase feature may be processed. In some embodiments, 468 may be implemented by the multi-time phase feature processing module 440. The processing may include generating a curve or table of a relationship between the multi-time phase feature and time phase by employing a technique such as fitting, interpolation, etc.

In 470, a multi-time phase feature or a processing result may be output. In some embodiments, 470 may be implemented by the output module 450. In some embodiments, 468 may be omitted, and the generated multi-time phase feature may be directly outputted.

Figure 5:
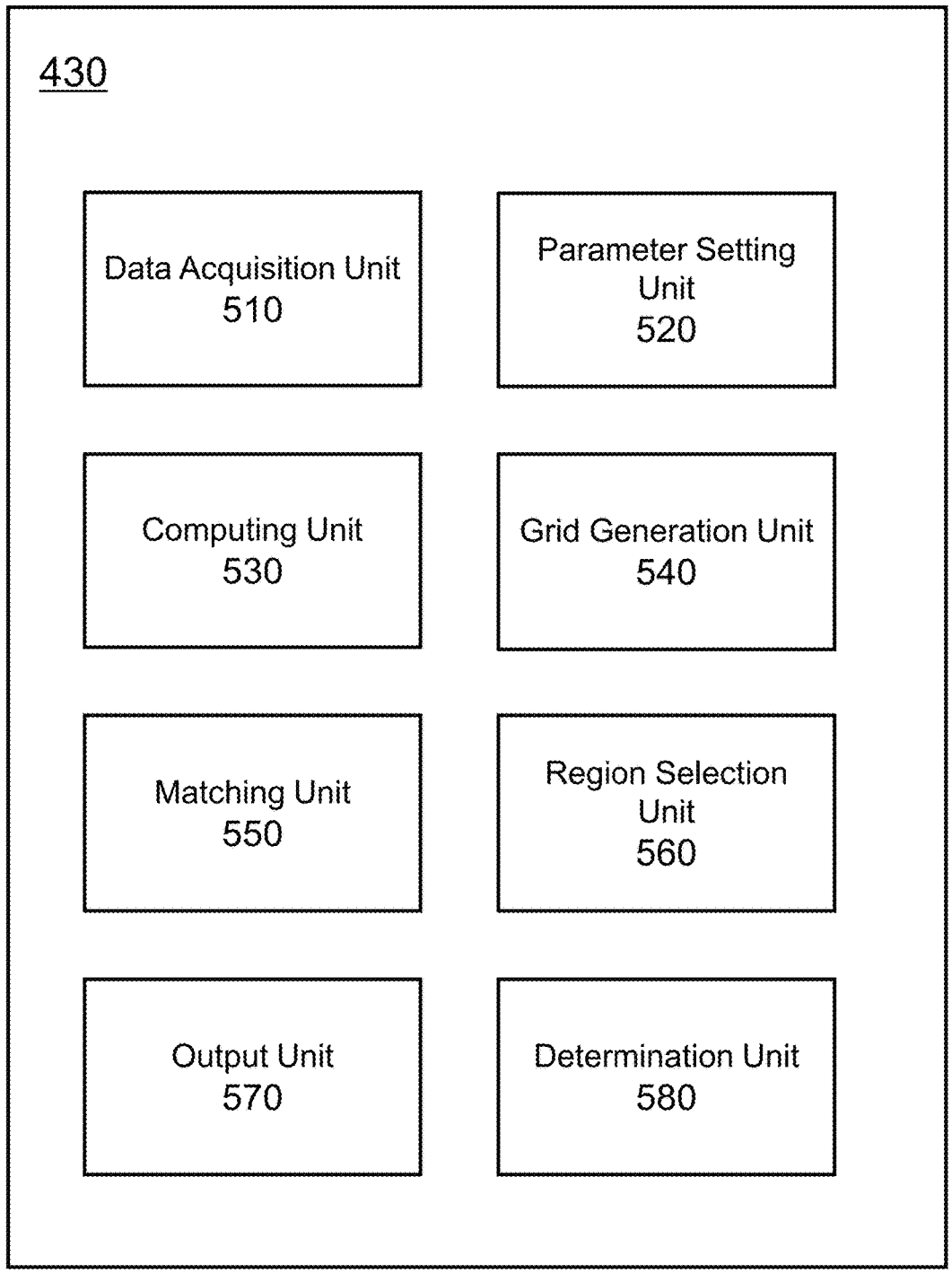
FIG. 5 illustrates a schematic diagram of an exemplary multi-time phase feature generation module according to some embodiments of the present disclosure.

FIG. 5 illustrates a schematic diagram of an exemplary multi-time phase feature generation module according to some embodiments of the present disclosure. The multi-time phase feature generation module 430 may include a data acquisition unit 510, a parameter setting unit 520, a computing unit 530, a grid generation unit 540, a matching unit 550, a region selection unit 560, an output unit 570, and a determination unit 580.

The data acquisition unit 510 may obtain data from other units of the multi-time phase feature generation module 430, other devices/modules of the blood flow condition analysis system 100, or external devices/modules. The data may include image data, object's features, user input, etc. The image data may include images or data of a blood vessel, a tissue, an organ of an object. The object's features may include heart rate, heart rhythm, blood pressure, blood velocity, blood viscosity, cardiac output, myocardial mass, vascular flow resistance, and other data related to the blood vessel, the tissue or the organ. In some embodiments, the image data and the object's features may be multi-time phase data. In some embodiments, the data acquisition unit 510 may obtain processed data (e.g., a reconstructed vascular model, etc.) from the storage device 130. In some embodiments, the data acquisition unit 510 may preprocess the obtained image data. The preprocessing may include image enhancement, image denoising, image smoothing, etc.

The parameter setting unit 520 may select a model. The parameter setting unit 520 may also set a parameter and a boundary condition of the model. The model selection may include selecting a suitable blood viscosity model and a velocity boundary model based on a lesion region that needs to be analyzed (e.g. a region of interest) and the object's features (e.g., blood viscosity, etc.). The blood viscosity model may include a Newtonian fluid model, a non-Newtonian fluid model, and other user-defined fluid model. The Newtonian fluid model may be used to simulate a region of an object with a constant blood viscosity. The non-Newtonian fluid model may be used to simulate a region of an object with a changing blood viscosity. The velocity boundary model may include a parabolic model, a hyperbolic model, an elliptical model, an average flow model, a Womersley distribution model, a Reynolds model, a mixture model, etc. In some embodiments, the parameter setting may include setting a parameter of a selected model, such as a blood viscosity coefficient of the Newtonian model, a blood density of the Newtonian model, time steps of a simulated computation, a time step length of the simulated computation, etc.

The setting of boundary conditions may include setting an initial condition and a limit condition of a boundary region. The boundary region may refer to an edge region of a region of interest. For example, if a selected region of interest is a blood flow region corresponding to a vascular region or a blood vessel, the boundary region may be an exit, an entrance, a vascular wall, etc. The set boundary condition may include blood pressure, blood velocity, flow resistance, pressure intensity, stress, etc. In some embodiments, an internal or external storage device of the storage device 130 or the blood flow condition analysis system 100 may include a database of boundary conditions. The user or the parameter setting unit 520 may set a boundary condition or select a boundary condition from the database of boundary conditions based on the object's features. In some embodiments, the user or the parameter setting unit 520 may select a low order coupling model as the boundary condition based on the region of interest. The low order coupling model may choose an empirical model of a region or a tissue as the boundary condition, wherein the region or the tissue may be coupled with the region of interest. The low order coupling model may be a second order model, a first order model, a zero order model (i.e., a centralized parameter model), or a combination thereof.

The computing unit 530 may be configured to compute data or information generated by other units of the multi-time phase feature generation module 430. In some embodiments, the computing unit may generate a corresponding model based on the image data. The model may be generated based on a model type and a parameter selected by the parameter setting unit 520. In some embodiments, the computing unit 530 may analyze and compute a model after reconstructing the model of a region of interest. The techniques used in the analysis and computation may include computed fluid dynamics, etc. In some embodiments, results of analysis and computation may include a physical state and a coefficient/parameter of a blood vessel, a tissue, or an organ. For example, a result of analyzing and computing the coronary artery model may include a hemodynamic parameter such as blood velocity, blood pressure, wall stress of the blood vessel, wall shear stress (WSS) of the blood vessel, fractional flow reserve (FFR), coronary flow reserve (CFR), or the like, or any combination thereof of the coronary artery.

In some embodiments, the information and data obtained by the computing unit 530 may be a multi-time phase information and data. The computing unit 530 may analyze and compute the multi-time phase information and data respectively. In some embodiments, the computing unit 530 may generate a relationship between the physical state and/or relevant coefficient/parameter and the time phase, according to the result of analysis and computation at different time phases. In some embodiments, the relationship may be represented by a curve or a table. Based on the curve or the table, the physical state and/or the coefficient/parameter of the region of interest at any time phase may be obtained. In some embodiments, the curve, the table, or the physical state and the coefficient/parameter of the region of interest at any time phase may be sent to an internal or external module/unit of the blood flow condition analysis system 100.

The grid generation unit 540 may generate grids of a model. In some embodiments, the grid generation unit 540 may generate a 2-dimensional or 3-dimensional grid of the model. For example, the grid generation unit 540 may generate a 2-dimensional grid in a boundary region (e.g., an entrance, an exit, etc.) of the model, and generate 3-dimensional grids in other regions of the model. The 3-dimensional grid may be reconstructed based on the 2-dimensional grid. The technique and process related to the grid generation may be found in FIG. 10, FIG. 12 and their corresponding descriptions.

The matching unit 550 may match multi-time phase data. In some embodiments, the matching unit 550 may correlate models at different time phases. The models at different time phases may be grid processed models. In some embodiments, the correlation of the models at different time phases may include: identifying characteristic regions of the models at different time phases; correlating the characteristic regions corresponding to different time phases. For example, if the models at different time phases are blood flow models (e.g., models of blood flow in a blood vessel of interest), the characteristic region may be an entrance region, a bifurcation region, an exit region, a stenosis region, etc. of the blood flow. Then the matching unit 550 may correlate the characteristic regions with each other. In some embodiments, the correlation of the models corresponding to different time phases may include registering the characteristic regions. In some embodiments, a characteristic region at different time phases may correspond to different numbers of grids. In some embodiments, the grids of the characteristic region at different time phases may be correlated by a specific algorithm or technique. For example, if multiple grids at the first time phase correspond to a single grid or fewer grids at the second time phase, the matching unit 550 may average the values of the multiple grids at the first time phase, and then correlate the averaged values with the value(s) of the grid(s) at the second time phase. In some embodiments, an initial value (e.g., an initial press intensity, an initial velocity, etc.) of internal grids (i.e., grids that is not include a boundary region of a grid model) may be set to be zero in a calculation at an initial time phase. In subsequent computations, a computation result of an internal grid at a previous time phase may be mapped or matched to a grid corresponding to the internal grid at current time phase. Then the computation result may be designated as an initial value at current time phase. In some embodiments, after a matching is completed, the matching unit 550 may prompt a user to determine whether the matching is accurate. In response to the determination that the matching is accurate, a subsequent process may be performed. In response to the determination that the matching is not accurate, the user may correct or adjust the matching result. The user may also select to re-match the grids.

The region selecting unit 560 may select a region of interest in image data. The region of interest may be selected solely by the region selecting unit 560 or selected based on user input. In some embodiments, the selected region of interest may be a blood vessel, a tissue, an organ, etc. The region selecting unit 560 may further segment the region of interest of the image. A technique of image segmentation may include a technique based on edges (e.g., a Perwitt operator, a Sobel operator, a gradient operator, a Kirch operator, etc.), a technique based on regions (e.g., a region growing technique, a threshold technique, a clustering technique, etc.), or other techniques based on fuzzy sets, a neural network, etc. The region selecting unit 560 may implement an automatic or semi-automatic segmentation. For example, if the selected region of interest is a coronary artery, an abdominal artery, a brain artery, a lower extremity artery, etc., the region selecting unit 560 may segment automatically. If the selected region is a blood vessel or other section that is difficult to be accurately segmented by machines, the region selecting unit 560 may segment semi-automatically with the user correcting in the segmentation process. In some embodiments, the region selecting unit 560 may perform the region selection and segmentation to a 3-dimensional model that is reconstructed based on image data.

The output unit 570 may send information, data, or a processing result generated by one or more units of the multi-time phase feature generation module 430 to other modules or units of the blood flow condition analysis system 100. For example, the output unit 570 may send a model generated by the computing unit 530 to the communication device 140 for displaying. As another example, the output unit 570 may send a model that is grid processed by the grid generation unit 540 to the storage device 130 for storing.

The determination unit 580 may implement a logic determination. For example, other modules or unit of the blood flow condition analysis system 100 may send a determination request to the determination unit 580. The determination unit 580 may determine a corresponding content based on the determination request. If a specific condition is met or a determination result is generated, the determination unit 580 may send the determination result or a corresponding operation instruction to a corresponding module or unit (e.g., a module or unit from which the determination request is obtained). For example, the determination unit 580 may determine whether a blood vessel to be analyzed by the region selecting unit 560 is abnormal (e.g., vascular stenosis, aneurysm, etc.) In response to the determination that the blood vessel is abnormal, the determination unit 580 may highlight (e.g., with a different color, etc.) the abnormal blood vessel and prompt a user to determine whether the abnormal blood vessel satisfies a need of the user. In response to the determination that the abnormal blood vessel satisfies the need of the user, a subsequent operation may be performed. In response to the determination that the abnormal blood vessel dose not satisfy the need of the user, the user may manually select the abnormal blood vessel and the subsequent operation may be performed. For example, the region selecting unit 560 may send the region of interest selected by the user and a region generated by the region selecting unit 560 to the determination unit 580. The determination unit 580 may determine whether the region of interest and the region generated by the region selecting unit 560 is the same. In response to the determination that the region of interest and the region generated by the region selecting unit 560 is the same, an instruction may be sent to the region selecting unit 560 for further segmentation processing. In response to the determination that the region of interest and the region generated by the region selecting unit 560 is different, the user may select and determine again by the communication device 140.

The above description of the present disclosure is provided for the purposes of illustration, and not intended to limit the scope of the present disclosure. For persons having ordinary skills in the art, modules may be combined in various ways, or connected with other modules as sub-systems. Various variations and modifications may be conducted under the teaching of the present disclosure. However, those variations and modifications may not depart the spirit and scope of this disclosure. For example, the above unit is described by taking a single phase as an example, but it should be noted that the data received, processed, or output by the unit may be multi-time phase data. For the multi-time phase data, the above unit may perform similar operations to data at different time phases to generate a multi-time phase feature. For example, the grid generation unit 530 may perform a corresponding grid processing to a multi-time phase model for generating a multi-time phase grid processed model. As another example, the parameter setting unit 520 may set a corresponding parameter or boundary condition of the multi-time phase model or data.

Figure 6:
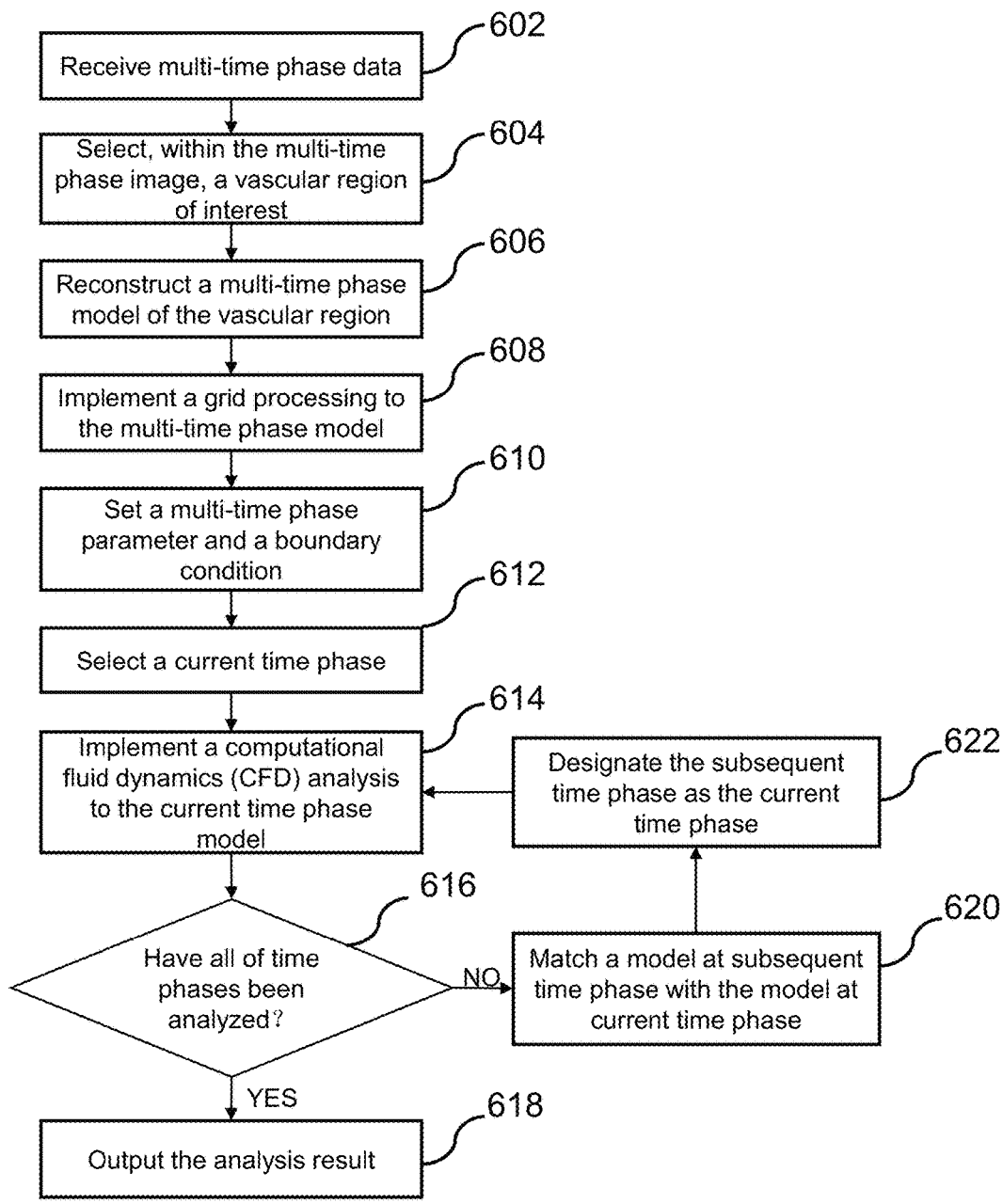
FIG. 6 is a flow chart illustrating a process for obtaining multi-time phase features according to some embodiments of the present disclosure.

FIG. 6 is a flow chart illustrating a process for obtaining multi-time phase features according to some embodiments of the present disclosure. In some embodiments, the process 600 may be implemented by the multi-time phase generation module 430.

In 602, multi-time phase data may be obtained. The multi-time phase data may include multi-time phase image data, multi-time phase object's features, etc. The multi-time phase image data may include images or data at multiple different time points of a blood vessel, a tissue, or an organ of an object. The multi-time phase object's features may include heart rate, heart rhythm, blood pressure, blood velocity, blood viscosity, cardiac output, myocardial mass, vascular flow resistance, and/or other data associated with the blood vessel, the tissues or the organ of the object. As showed in FIG. 7, 702 may include heart images at three time phases. The 704 may be a blood pressure curve of an object in a cardiac cycle. In some embodiments, the multi-time phase image may include at least part of the same blood vessel, issue, or organ. In some embodiments, the obtained multi-time phase image may be preprocessed. The preprocessing may include image enhancement, image denoising, image smoothing, etc.

In 604, a vascular region of interest may be selected within the multi-time phase image. The region of interest may be selected solely by the region selecting unit 560, or selected based on user input. The selected regions of interest of images at different time phases may be the same. In some embodiments, the selected region of interest may be further segmented. The technique of image segmentation may include a technique based on edges (e.g., a Perwitt operator, a Sobel operator, a gradient operator, a Kirch operator, etc.), a technique based on regions (e.g., a region growing technique, a threshold technique, a clustering technique, etc.), or other techniques based on fuzzy sets, a neural network, etc. The segmentation may be automatic or semi-automatic. For example, if the selected region of interest is a coronary artery, an abdominal artery, a brain artery, a lower extremity artery, etc., the automatic segmentation may be performed. If the selected region is a blood vessel or other section that is difficult to be accurately segmented by machines, the semi-automatic segmentation may be performed with the user correcting in the segmentation process. In some embodiments, the images at different time phases may be segmented in sequence or simultaneously.

Figure 7:
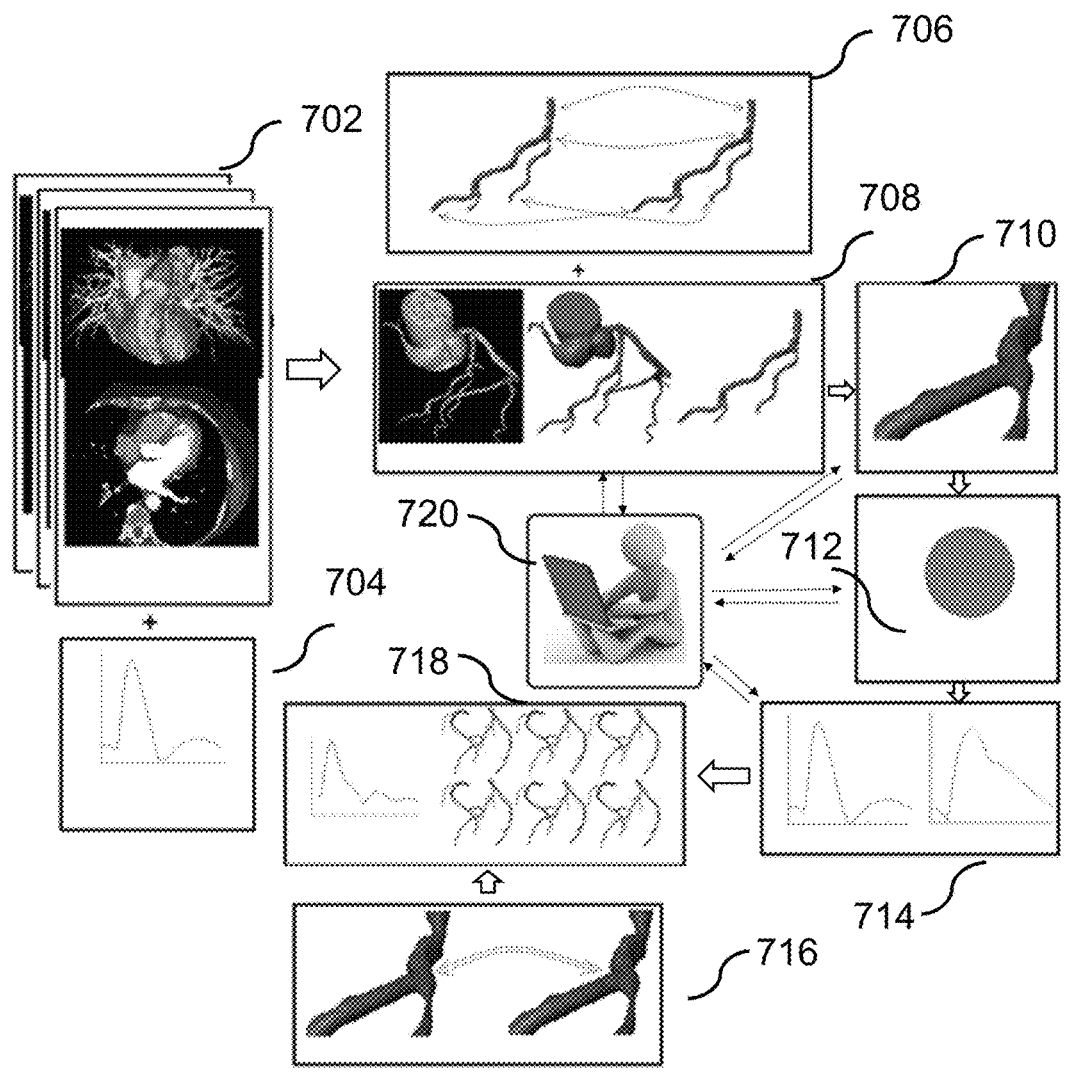
FIG. 7 is a schematic diagram illustrating a process for obtaining multi-time phase features according to some embodiments of the present disclosure.

In 606, a multi-time phase model of a vascular region may be reconstructed. The multi-time phase model may be a vascular model, or a blood flow model. The vascular region may be a region of a coronary artery blood vessel, an abdominal artery blood vessel, a brain artery blood vessel, a lower extremity artery blood vessel, etc. In some embodiments, the vascular region may be part or all of the blood vessel. For example, the vascular region may be an entire coronary artery model, a left coronary artery model, a right coronary artery model, or a coronary branch model (e.g., a left anterior descending (LAD), a left circumflex (LCX), a diagonal branch, etc.). As shown in FIG. 7, 708 from left to right is an image, a model, and a segmented model, respectively. In some embodiments, a suitable blood viscosity model and a velocity boundary model may be selected based on a lesion region that needs to be analyzed (e.g., a region of interest) and an object's features (e.g., blood viscosity, etc.). The blood viscosity model may include a Newtonian fluid model, a non-Newtonian fluid model, and other user-defined fluid model. The velocity boundary model may include a parabolic model, a hyperbolic model, an elliptical model, an average flow model, a Womersley distribution model, a Reynolds model, a mixture model, etc. In some embodiments, models corresponding the images at different time phases may be constructed respectively.

In 608, a grid processing may be implemented to the reconstructed multi-time phase model. In some embodiments, 2-dimensional grids may be generated at a boundary region (e.g., an entrance, an exit, etc.) of the model, while 3-dimensional grids may be generated at other regions of the model. The 3-dimensional grids may be reconstructed based on the 2-dimensional grids. As showed in FIG. 7, 710 may be obtained by grid processing the model 708. The technique and process related to the grid generation may be found in FIG. 10, FIG. 12 and their corresponding descriptions.

In 610, a multi-time phase parameter and a boundary condition may be set. In some embodiments, the setting of the parameter may include setting a parameter of a selected model, such as velocity u, density ρ, blood pressure P, cross-sectional area S, etc. The setting of the boundary condition may include setting an initial condition and a limit condition of a boundary region. The boundary region may refer to an edge region of a region of interest. For example, the boundary region may be an exit, an entrance, a vascular wall, or the like of a blood vessel. The set boundary condition may include blood pressure, blood velocity, flow resistance, pressure intensity, stress, etc., of the boundary region. In some embodiments, a low order coupling model may be selected as the boundary condition based on the region of interest. The low order coupling model may choose an empirical model of a region or a tissue as the boundary condition, wherein the region or the tissue may be coupled with the region of interest. The low order coupling model may be a second order model, a first order model, a zero order model (i.e., a centralized parameter model), or a combination thereof of the low order models. As shown in FIG. 7, 712 may be an embodiment of selecting a model and setting a parameter. The 714 may be an embodiment of setting a boundary condition.

In 612, a current time phase (also referred as an initial time phase if first selected) may be selected. In some embodiments, the initial time phase may be selected based on some specific rules. For example, a time phase that a model changes slowly or comparably slowly (e.g., a time phase that is closest to a beginning of heart contraction or an end of heart diastolic) may be selected as the initial time phase for a coronary artery. The initial time phase may be selected by a machine (e.g., the multi-time phase feature generation module 430) or a user. If the machine and the user do not or cannot select an initial time phase, an arbitrarily selected time phase or a first time phase received by the multi-time phase feature generation module 430 may be designated as the initial time phase.

In 614, a current time phase (also referred as an initial time phase if first selected) may be analyzed. For example, the initial time phase may be implemented by a computational fluid dynamics (CFD) analysis. According to a predetermined model, boundary condition and parameter, hemodynamic parameters of a 3-dimensional vascular model may be obtained. A control equation based on Euler equations, Navier-Stokes equations, or a Lattice Boltzmann method may be used in obtaining the parameters. A discretization technique such as a finite difference technique, a finite volume technique, a finite element technique, a boundary element technique, a spectral technique, a Lattice Boltzmann technique, a meshless technique, or the like, or any combination thereof may be used in obtaining the parameters. A fluid of the flow field computation that used in obtaining the parameters may be viscous or non-viscous. The fluid may be compressible or incompressible. The fluid may be a laminar flow or a turbulent flow. The fluid may be a steady flow or an unsteady flow. A corresponding control equation or simulation method may be selected based on physical features of the simulated fluid. For example, the Euler equations or the Lattice Boltzmann method may be selected for the flow field computation of the non-viscous fluid, while the Navier-Stokes equations or the Lattice Boltzmann method may be selected for the flow field computation of the viscous fluid. For example, a computation of the computational fluid dynamics (CFD) for the coronary artery may use the Navier-Stokes equations:

$$\frac{\partial \rho}{\partial t} + \nabla \cdot (\rho u) = 0, \text{ and} \tag{1}$$

$$\frac{\partial \rho u}{\partial t} + \nabla \cdot (\rho u u) = \nabla \cdot \sigma. \tag{2}$$

Here, ρ may denote the blood density, u may denote the blood velocity, t may denote the time, and σ may denote the blood stress (which is determined by the blood pressure p and the blood viscosity). In some embodiments, an initial velocity of the model may be set to zero in computation at the initial time phase. In the subsequent computations, the initial velocity of the model may not be set to zero, and grids in adjacent time phases may be matched. A computation result at a previous phase may be assigned to the corresponding grid at current time phase as an initial value.

The analysis result may include a physical state and a coefficient/parameter of any region or point of the model at current time phase. For example, a result of analyzing the coronary artery model may include a hemodynamics parameter at any region or point, such as blood velocity, blood pressure, wall stress of the blood vessel, wall shear stress (WSS) of the blood vessel, fractional flow reserve (FFR), coronary flow reserve (CFR), or the like, or any combination thereof. As shown in FIG. 7, 718 may illustrate an analysis and computation of hemodynamics.

In 616, it may be determined whether all of time phases have been computed. In response to the determination that all of time phases have been computed, 618 may be implemented. In response to the determination that not all of time phases have been traversed, 620 may be implemented.

In 618, the analysis result may be outputted. For example, the analysis result may be sent to other modules or units of the blood flow condition analysis system 100. In some embodiments, the analysis result may be post-processed. The post-processing may include generate a curve or table of a relationship between the analysis result of the model and time phase. According to the curve or table of the relationship, the post-processing may further include outputting an estimated value of the analysis result at any time phase. A process and result of the post-processing may be found in FIG. 13 and its corresponding description. In some embodiments, the multi-time phase processing module 440 may compare the generated multi-time phase computation result (e.g., a vascular condition) and a reference result to generate a comparison result. As shown in FIG. 7, 716 may illustrate a result of the post-processing. A process and result of the post-processing may be found in FIG. 13 and its corresponding description. In some embodiments, 618 may further include comparing the generated multi-time phase computation result (e.g., a vascular condition) and a reference result to generate a comparison result. The reference result may be stored in the storage device 130 or the network 180, or input by a user. In some embodiments, the reference result and the related comparison result may be stored in a table. For example, if the computation result is the blood velocity, the reference result may be a relationship between a range of the blood velocities and their corresponding risk. The degree of risk may be divided into normal, warning, dangerous, extremely dangerous, etc. In some embodiments, the user may input the relationship manually based on clinical experiences. In some embodiments, the comparison may be a comparison of the computation results of a same object at different time periods.

In 620, a model at a subsequent time phase may be matched with a model at a current time phase. In some embodiments, a process of matching models at different time phases may include: identifying characteristic regions of the models at different time phases; and correlating the characteristic regions corresponding to different time phases. In some embodiments, the characteristic region may be an entrance, a bifurcation region, an exit, a stenosis region, a dilation region, etc. of the blood flow. The 620 may include correlating the characteristic regions corresponding to different time phases. In some embodiments, the correlation of the models corresponding to different time phases may include registering the characteristic regions. As shown in FIG. 7, 706 may be an embodiment of correlating a model and characteristic regions of the model. In some embodiments, a characteristic region at different time phases may correspond to different numbers of grids. In some embodiments, the grids of the characteristic region at different time phases may be correlated by a specific algorithm or method. For example, if multiple grids at the first time phase correspond to a single grid or fewer grids at the second time phase, the matching unit 550 may average the values of the multiple grids at the first time phase, and then correlate the averaged values with the value(s) of the grid(s) at the second time phase. The corresponding grid values may include defining the grid value at the first time phase as an input value of the grid corresponding to the second time phase.

In 622, the subsequent time phase may be designated as the current time phase, and 614 may be implemented.

The above description of the present disclosure is provided for the purposes of illustration, and not intended to limit the scope of the present disclosure. For persons having ordinary skills in the art, modules may be combined in various ways, or connected with other modules as subsystems. Various variations and modifications may be conducted under the teaching of the present disclosure. However, those variations and modifications may not depart the spirit and scope of this disclosure. For example, 606 may be implemented before 604. A model of the entire region may be constructed based on image data, then a region of interest may be selected and segmented from the model.

Figure 8:
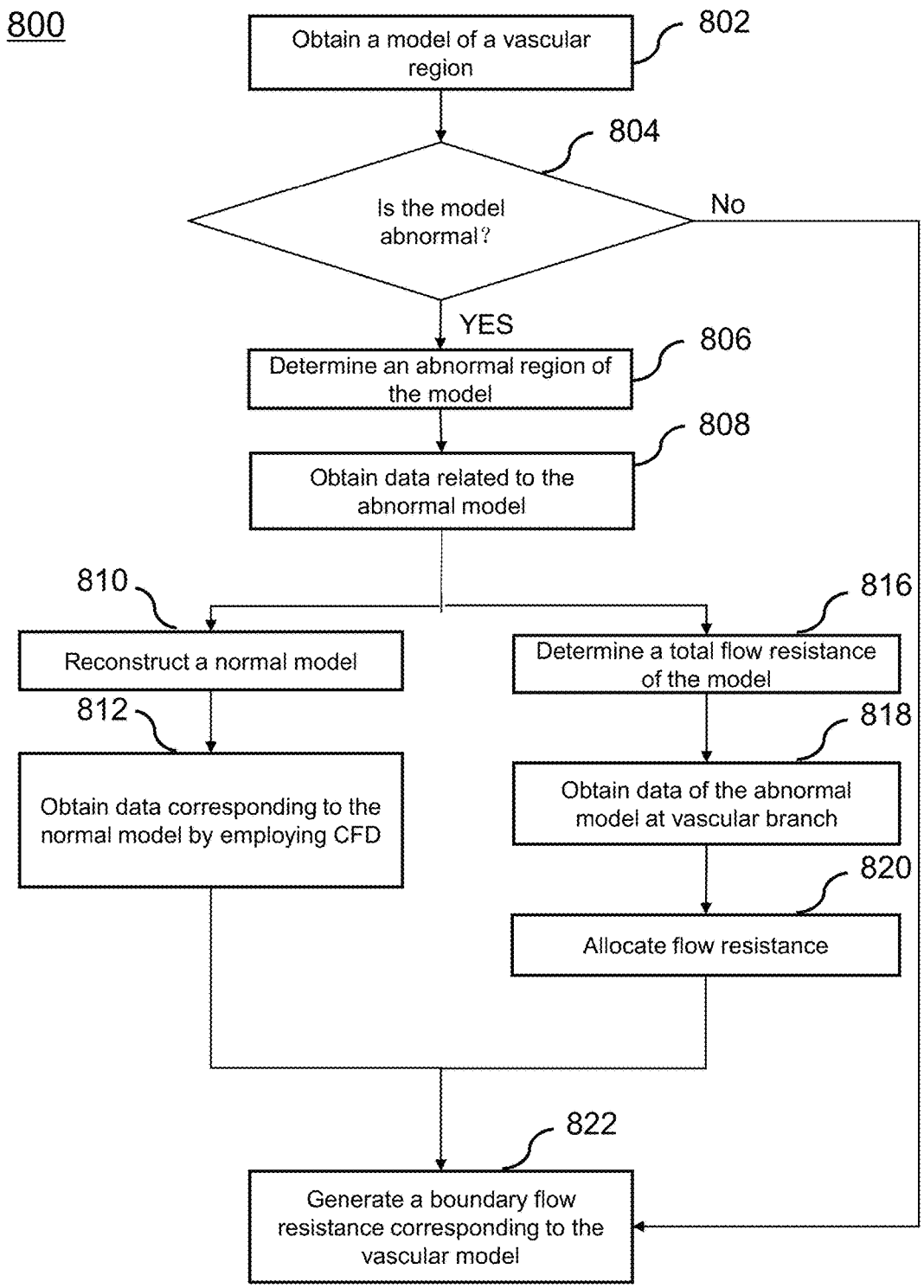
FIG. 8 is a flow chart illustrating a process for setting a boundary condition according to some embodiments of the present disclosure.

FIG. 8 is a flow chart illustrating a process for setting a boundary condition according to some embodiments of the present disclosure. In some embodiments, 610 may correspond to the process 800. In some embodiments, process 800 may be implemented by the parameter setting unit 520.

In 802, a model of a vascular region may be obtained. In some embodiments, the model may be obtained by 606. The model may be a vascular model or a blood flow model. The vascular region may be a region of coronary artery, abdominal artery, brain artery, lower extremity artery, etc. In some embodiments, the vascular region may be part or all of the region. For example, the vascular region may be an entire coronary artery model, a left coronary artery model, a right coronary artery model, or a coronary branch model (e.g., a left anterior descending (LAD), a left circumflex (LCX), a diagonal branch, etc.). In some embodiments, the model may be a vascular region in a mask form. In some embodiments, the model may be a grid processed vascular model.

Figure 9:
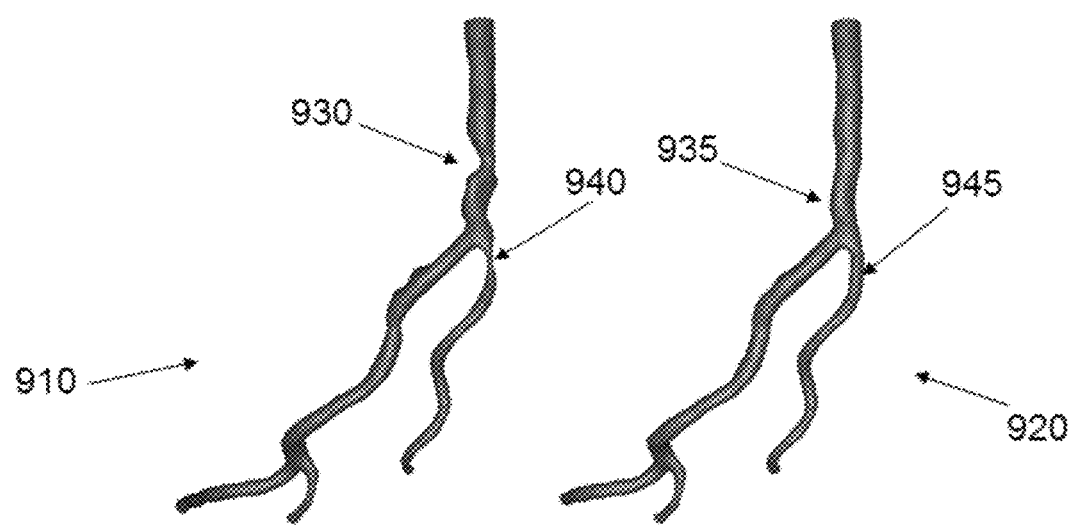
FIG. 9 is a schematic diagram of a blood flow module according to some embodiments of the present disclosure.

In 804, it may be determined whether the model of the vascular region is abnormal. The abnormal condition may include a vascular stenosis, a thrombus, a vascular dilation, an angioma, etc. As shown in FIG. 9, model 910 may be a coronary artery model with two narrow regions 930 and 940.

The model 920 may be a normal coronary artery model, and regions (e.g., 935, 945) corresponding to 930, 940 are not narrow. In some embodiments, 804 may include extracting a centerline of the vascular region model. In some embodiments, the vascular centerline may refer to an imaginary line located in the blood vessel along the trend of the blood vessel. The vascular centerline may include a set of one or more pixels (or voxels) in the blood vessel. In some embodiments, the vascular centerline may include a line of a set of one or more pixels (or voxels) in or near the center of the blood vessel. In some embodiments, the vascular center may include one or more vascular endpoints. The vascular centerline may be a path between the endpoints. In some embodiments, an exemplary method of extracting the vascular centerline may refer to a PCT application No. PCT/CN2016/097294, filed on Aug. 30, 2016, an entire content of which are hereby incorporated. A plurality of feature points may be predetermined along the vascular centerline. A cross-sectional area of the model at the feature points may be obtained. According to the area of the feature point, whether the model is abnormal may be determined. For example, if there exists an abnormal reduction (for example, a feature point with a low cross-sectional area locates between two feature points with normal cross-sectional areas) in the obtained cross-sectional areas of the feature points, the model may be determined to have a stenosis or thrombus. In some embodiments, a number of the feature points may be sufficient such that the change of the cross-sectional areas can determine whether there is an abnormal condition. For example, the distance between selected adjacent feature points is less than the length of the narrow region. In response to the determination that the model is normal, 822 may be performed. In response to the determination that the model is abnormal, 806 may be performed.

In 806, an abnormal region may be determined. For example, according to a change of cross-sectional areas of a model that is abnormal (also be referred as an abnormal model), possible narrow or dilated regions may be determined and marked. The narrow or dilated region may be a region of a blood vessel where the local cross-sectional area is minimum or maximum, or a region where the cross-sectional area changes dramatically. In some embodiments, the determined abnormal region may be sent to the user. In response to the determination that the abnormal region is not accurate, the user may modify the abnormal region. For example, the user may select manually one or more points or a range of the abnormal model as the abnormal region.

In 808, data related to the abnormal model may be obtained. The data may include a blood velocity of the entrance of a vascular entrance, a blood flow volume of the entrance, a blood pressure of the entrance, a flow resistance of the entrance, a number of branches, a number of entrances, a number of exits, a blood viscosity, a blood density, etc. of the blood vessel. In some embodiments, the blood flow volume of the vascular entrance may be obtained based on a parameter or feature related to a tissue or organ that connects to the blood vessel. For example, the blood flow volume of the coronary artery entrance may be estimated by a cardiac output. The cardiac output is obtained by analyzing volume changes of a heart chamber at a cardiac cycle. Some empirical physiological laws may also be employed to estimate the physical quantities. For example, the blood flow volume of the coronary artery is proportional to the myocardial mass, i.e. $Q \propto Q_o M^\alpha$, wherein $Q$ may denote the blood flow volume of the coronary artery, $Q_o$ may denote a constant, M may denote the myocardial mass, and the exponent $\alpha$ may denote a predefined variation factor. In some embodiments, the myocardial mass M may be obtained by a noninvasive technique, such as by multiplying a myocardial volume to a myocardial density. In some embodiments, the blood pressure of the coronary artery entrance may be measured by a blood-pressure meter, etc.

In 810, a normal model may be reconstructed based on the abnormal model. In some embodiments, only determined abnormal regions are reconstructed, and other regions are unchanged. In some embodiments, the methods of reconstruction include lofting or stretching the blood vessel based on diameters or centerlines to generate a normal region. In some embodiments, the reconstruction technique may include dilating or narrowing the abnormal region. The dilated vascular cross-sectional area may not be larger than vascular cross-sectional areas of adjacent regions. The narrowed vascular cross-sectional area may not be smaller than a vascular cross-sectional areas of adjacent regions. In some embodiments, the adjacent regions of the reconstructed abnormal region may be smoothed to avoid significant mutations. In some embodiments, the reconstructed model may be sent to the user. In response to the determination that the reconstruction is not accurate, the user may modify a part or all of the reconstructed normal model. For example, the user may locally dilate, narrow, smooth the reconstructed normal model.

In 812, data corresponding to the normal model may be obtained. The data may include a boundary condition, a flow resistance of each entrance and exit, etc. The boundary condition may include the blood pressure, the velocity, the flow volume, etc. of the entrance and the exit. In some embodiments, the blood pressure and velocity of the entrance may be obtained in 808. The flow volume of the entrance may be obtained by computation. For example, assuming that the flow distribution of a branch vessel is positively correlated with the branch diameter, i.e. $Q \propto d^k$, wherein d denotes the average diameter of a proximal branch vessel (i.e., a region close to the branch), and k denotes an amplification factor. Then, the flow volume may be allocated in branches of blood vessel in accordance with the positive relationship from the entrance, until the flow volume of the entrance is allocated to all the branches. Based on the normal model and the boundary condition, a computational fluid dynamics (CFD) simulation may be computed to obtain a flow resistance (i.e., a ratio of the entrance pressure to the entrance flow volume) at each entrance of the normal model.

In 816, a total flow resistance of the model may be obtained. The total resistance may be computed by the following formula:

$$R = \frac{P_{inlet}}{Q}, \quad (3)$$

wherein R denotes the total resistance of a model, $P_{inlet}$ denotes the blood pressure intensity of an entrance, and Q denotes the flow volume of the entrance. $P_{inlet}$ and Q may be obtained in 808, and is not repeated here.

In 818, the diameter of each proximal branch vessel at each level (e.g. a first level may represent branches at a first bifurcation, and a second level may represent branches at a subsequent bifurcation of the first branches) may be determined by analyzing the vascular centerline, the vascular cross-sectional area, and the vascular abnormal region.

In 820, the flow resistance may be allocated based on the size of the diameter of the normal model. The flow resistance may be allocated based on the following formula:

$$R_i^j = (d_i^{-k} \cdot \Sigma_i d_i^k) \cdot R^{j-1}, \quad (4)$$

wherein d denotes the diameter, i denotes the number of a bifurcation blood vessel at the current level, j denotes the level that the current flow resistance assignment belongs to, and k denotes an allocation exponent of the flow resistance (for example, k of the coronary artery may be set to 2.7).

In 822, a boundary resistance corresponding to an actual vascular model may be generated. In some embodiments, the boundary resistance corresponding to an actual vascular model may be obtained based on a boundary resistance corresponding to the normal model. For example, the boundary resistance corresponding to an actual vascular model may be the same as the boundary resistance corresponding to the normal model. In some embodiments, the boundary resistance of the vascular model may be allocated based on a method described in 820.

Figure 10:
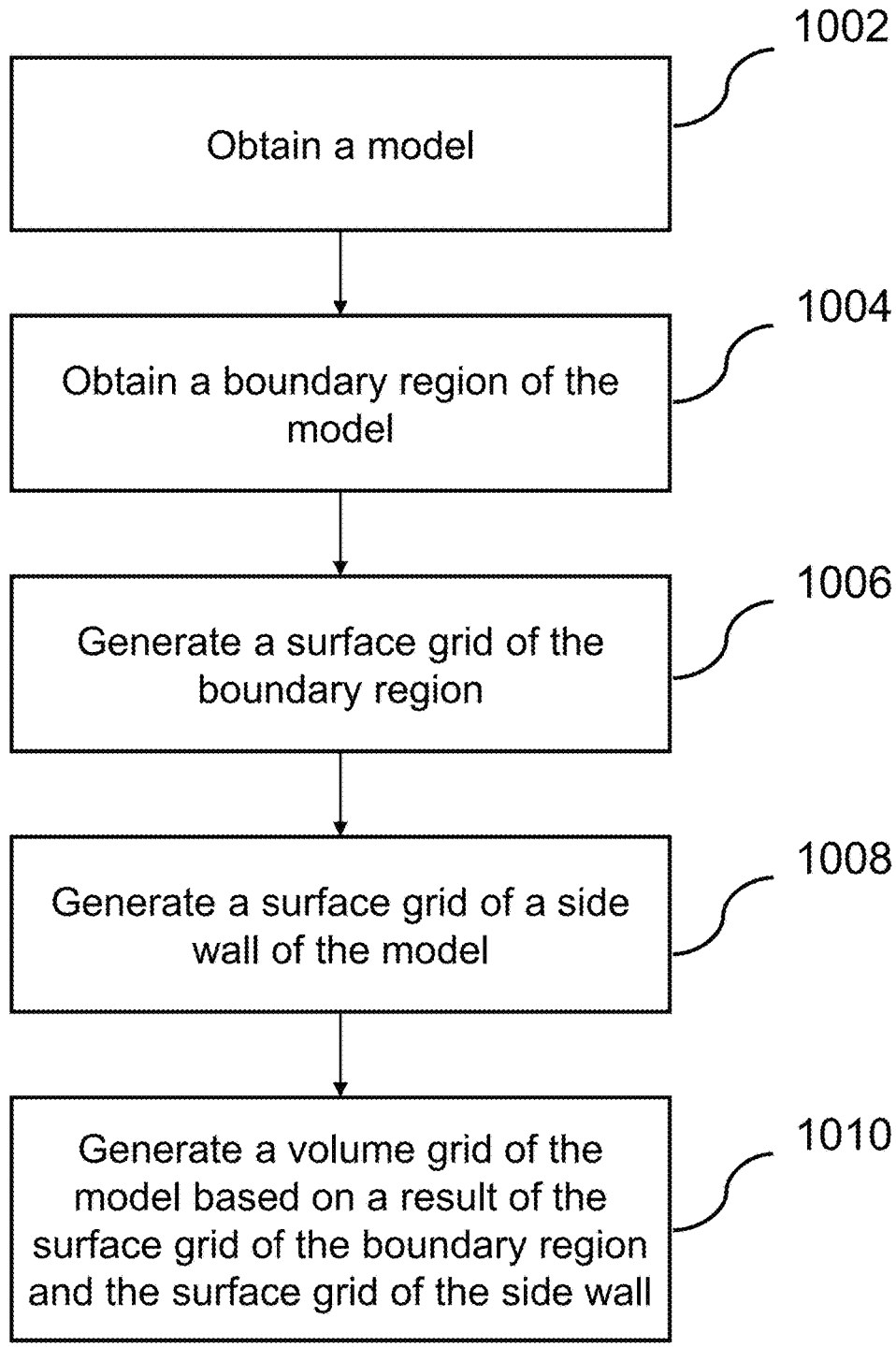
FIG. 10 is a flow chart illustrating a process for a grid division according to some embodiments of the present disclosure.

FIG. 10 is a flow chart illustrating a process for a grid division according to some embodiments of the present disclosure. In some embodiments, process 1000 may correspond to 608. The process 1000 may be implemented by the grid generation unit 540.

Figure 11:
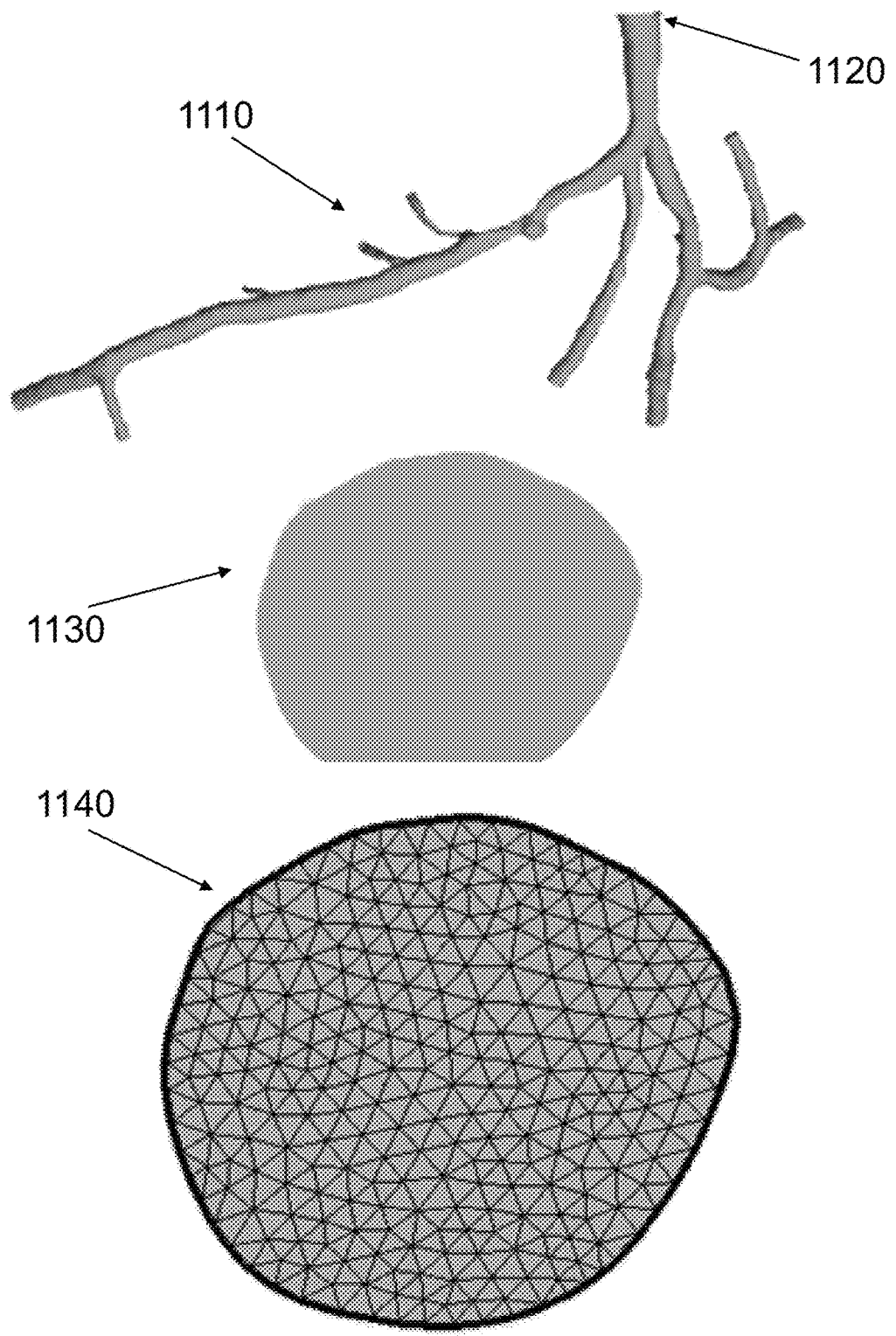
FIG. 11 illustrates a schematic diagram of a process for a grid division of a boundary region according to some embodiments of the present disclosure.

In 1002, a model may be obtained. The model may be described in some other embodiments of the present disclosure, such as a reconstructed model of a blood vessel/blood flow, a tissue/organ, or other region of interest of an object. As shown in FIG. 11, 1110 may be a coronary artery blood flow model, e.g., model 1110 may represent the blood flow of the coronary vessel. Without considering conditions such as vessel wall thickness, vascular occlusion, etc., the model 1110 may also approximately represent a coronary vascular model.

In 1004, a boundary region of the model may be obtained. If the model corresponds to a blood vessel or a blood flow related to the blood vessel, the boundary region may be an exit, an entrance, a vascular wall, etc. As shown in FIG. 11, an entrance 1120 of the model 1110 may be determined to be a boundary region of the model 1110 in 1004.

In 1006, surface grids of a determined boundary region may be generated (also referred to as a 2-dimensional grid division or 2D grid process). The surface grid division may include using grids to divide a surface corresponding to the boundary region. Algorithms used in the grid division may include a triangular grid division, a quadrilateral grid division, a hexagonal grid division, or the like, or a combination thereof. Exemplary grid division algorithms may include a Loop algorithm, a butterfly subdivision algorithm, a Catmull-Clark algorithm, a Doo-Sabin algorithm, a Delaunay triangular division algorithm, etc. Embodiments of the grid division technique may refer to FIG. 12 and its corresponding description. As shown in FIG. 11, 1130 may be cross-sectional diagram of an entrance of the model 1110, and 1140 may be an exemplary result of the grid division 1130.

In 1008, surface grids of a side wall of the model may be generated. In some embodiments, the side wall and boundary region may be divided by different grid division techniques. For example, the side wall may be divided by a surface grid subdivision algorithm. The surface grid subdivision algorithm may include a mapping technique, an automatic grid generation technique, etc. The mapping technique may include: mapping the side wall to a surface; dividing the surface by a 2-dimensional grid division method; and mapping the divided grids to the side wall. The automatic grid generation technique may include: dividing the side wall into multiple approximate surfaces according to the curvature of different regions of the side wall; and then implementing the 2-dimensional grid division. The surface grid division may be found elsewhere in the present disclosure, such as FIG. 12 and its corresponding descriptions.

In 1010, volume grids of the model may be generated (also referred to as a 3-dimensional grid division or 3-D grid process) based on the results of the surface grid divisions of the boundary region and the side wall. The volume grid division may include dividing the model into 3-dimensional grids. The 3-dimensional grids may include a tetrahedral grid, a hexahedral mesh, a prismatic grid (i.e., a boundary layer grid), a mixture grid of tetrahedron and hexahedron, a Cartesian grid, a ball filling grid, etc. In some embodiments, 1004 through 1008 may be omitted, e.g., the model may be directly divided by volume grids.

Figure 12:
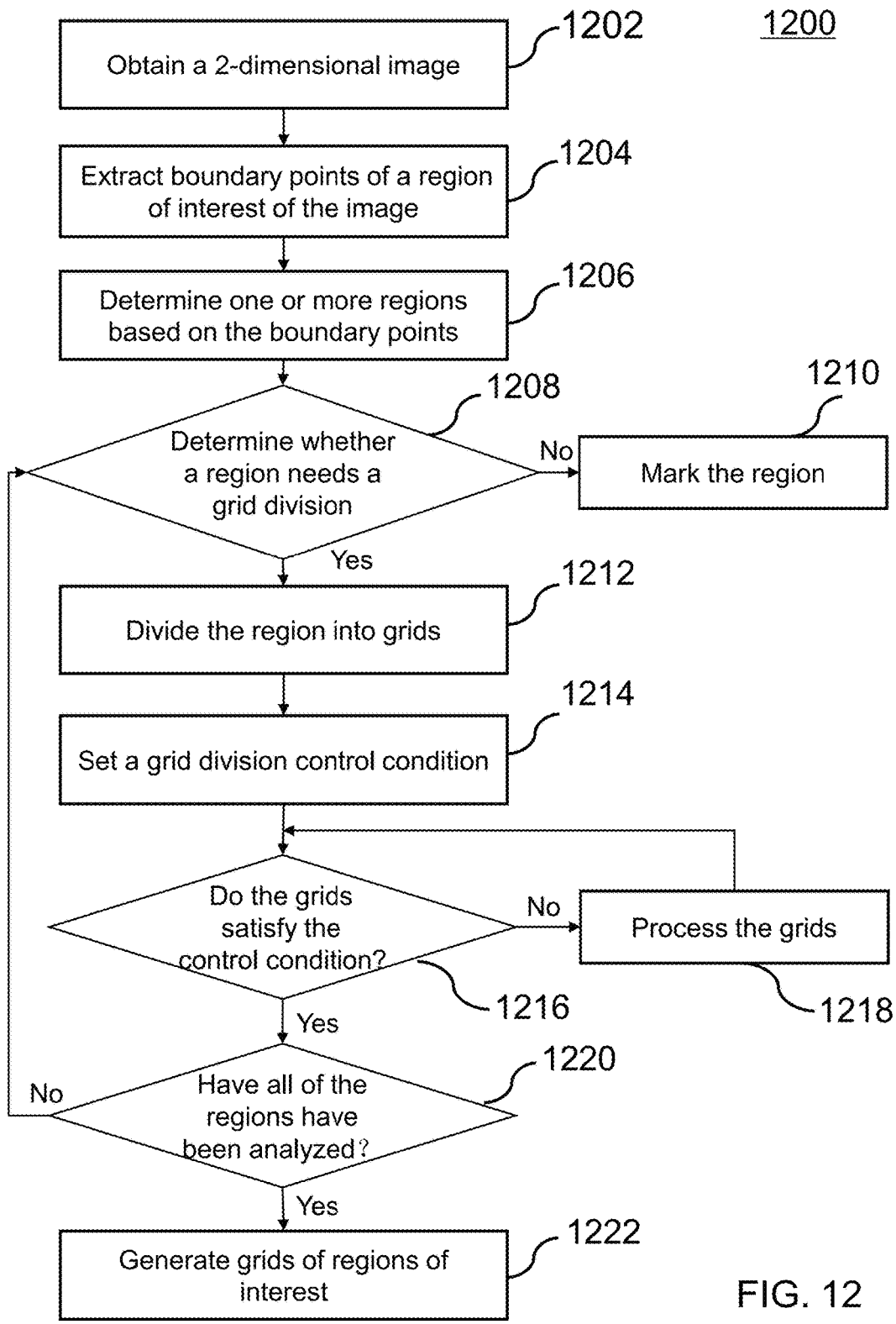
FIG. 12 illustrates a flow chart of a process for a grid division according to some embodiments of the present disclosure.

FIG. 12 illustrates a flow chart of a process for a grid division according to some embodiments of the present disclosure. In some embodiments, the process 1200 may be implemented by the multi-time phase feature generation module 430. In some embodiments, 608 in the FIG. 6, 1006 in FIG. 10, etc., may be implemented based on the process 1200.

In 1202, a 2-dimensional image may be obtained. In some embodiments, the 2-dimensional image may be obtained by the data acquisition unit 510. In some embodiments, the 2-dimensional image may be a 2-dimensional medical image, or an interesting region of the user (e.g., a coronary vascular region, a brain region, etc.). Merely by way of example, the 2-dimensional image may be a CT image, an MRI image, a PET image, or the like. The 2-dimensional image may be presented in grayscale or color. In some embodiments, the 2-dimensional image may be a 2-dimensional presentation of a model at a time phase. For example, the 2-dimensional image may be an image related to a boundary region of model in 1006. More particularly, the 2-dimensional image may display an entrance/exit region of a vascular model (for example, as shown in FIG. 9). The 2-dimensional image may be an image reconstructed by an image processing device (e.g., the processing device 120). The 2-dimensional image may be an image obtained from a local storage device or an external storage device (e.g., the storage device 130).

In 1204, the grid generation unit 540 may extract boundary points of a region of interest of a 2-dimensional image. In some embodiments, extracting boundary points from the region of interest of the 2-dimensional image may include segmenting the region of interest; and extracting the boundary points of the segmented region of interest. A technique of segmenting the region of interest may be found elsewhere in the present disclosure. In some embodiments, the boundary points of the region of interest may include one or more pixels in the boundary of the region of interest (also referred to as "boundary pixels"). For example, the boundary points at the cross-section of a coronary artery may include one or more boundary pixels located in the wall of coronary artery. In some embodiments, the boundary pixels of the region of interest may be continuous, partially continuous, or discontinuous. The term "continuous" may refer to that a boundary pixel is adjacent to at least one or more other boundary pixels. The extracted boundary points may be stored in one or more storage devices (e.g., the storage device 130, the storage module 260, etc.). The boundary points may be used by the grid generation unit 540 or other unit/module with a data analysis function in subsequent processes. The exemplary i boundary point may include the position of the boundary point, the number of the boundary point, or the like, or any combination thereof.

In 1206, one or more regions may be determined based on the boundary points. In some embodiments, the determination of the one or more regions may be implemented by the grid generation unit 540. The one or more regions may be formed by sequentially connecting the boundary points of the region of interest. Merely by way of example, the determination of one or more regions may include determining an initial boundary pixel of the region of interest (for example, a point with the smallest x/y coordinates in the contour pixel may be selected as the initial boundary pixel). The boundary pixels of the region of interest may be sorted in a clockwise or counterclockwise direction. Starting from the initial boundary pixel, a previous boundary pixel may be connected to a subsequent boundary pixel by a line to form a short edge. If the previous boundary pixel is connected to the initial boundary pixel, and a short edge is formed, a closed boundary curve may be formed. In some embodiments, the region of interest may be located in a closed boundary curve. For example, the region of interest of the model entrance 1140 in FIG. 11 (i.e., the region of grid division) may be located in the boundary curve. In some embodiments, the region of interest may be a region located between two closed boundary curves. For example, the region of interest may be a 2-dimensional ring structure, or a structure equivalent to the 2-dimensional ring topology. The information of one or more regions (e.g., a grid curve corresponding to the region) may be stored in one or more storage devices (e.g., the storage device 130, the storage module 260, etc.). The information of one or more regions may be used by the grid generation unit 540 or other unit/module with a data analysis function in subsequent processes.

In 1208, it may be determined whether a region needs a grid division. In some embodiments, the determination may be implemented by the determination unit 580. In response to the determination that the region needs no grid division, the process 1200 may proceed to 1210. In response to the determination that the region needs a grid division, the process 1200 may proceed to 1212. In some embodiments, a condition determined by the determination unit 580 may include whether the region is a region of interest. In response to the determination that the region is a region of interest, the grid division may be determined to be needed. As described elsewhere in this disclosure, the region of interest may include a region that needs a blood state analysis, e.g., a region where blood flows in a specific blood vessel.

In 1210, the region that needs or does not need to be divided may be marked. In some embodiments, the marking of the region may be implemented by the grid generation unit 540. In some embodiments, the marking may be performed in a form of a computer readable code or an executable instruction. The marked region may be stored in one or more storage devices (e.g., the storage device 130, the storage module 260, etc.). The marked region may be read by the grid generation unit 540 or other unit/module with a data analysis function in subsequent processes. For example, the marked region may be removed if a grid division is performed.

In 1212, the region may be divided into grids. In some embodiments, the grid division may be implemented by the grid generation unit 540. In some embodiments, grid division may be performed based on the boundary points of the region. Algorithms used in the grid division may include a triangular grid division, a quadrilateral grid division, a hexagonal grid division, or the like, or a combination thereof. Exemplary grid division algorithm S may include a Loop algorithm, a butterfly subdivision algorithm, a Catmull-Clark algorithm, a Doo-Sabin algorithm, a Delaunay triangular division algorithm, etc. As another example, the grid generation unit 540 may classify the boundary points of the region into different subsets, and sequentially grid-divide the boundary points of each subsets. The grid generation unit 540 may then combine the grid division of the subsets to form a grid division of the region. Particularly, all of the boundary points of the region may be ordered according to the x/y coordinates (for example, the boundary points may be firstly arranged in a non-descending order with respect to the x-coordinates, and then be arranged in a non-descending order with respect to the y-coordinates for the points of the same x-coordinates). The ordered boundary points may be divided into a subset A and a subset B based on their quantity. A Delaunay triangular division of the two subsets may be completed respectively. Then the Delaunay triangular division of the subset A and the subset B may be combined to generate a Delaunay triangular division of all of the boundary points. In some embodiments, the grid division may also include superimposing the boundary curve of the region on the divided grids. In this case, the boundary curve of the region may be maintained in the divided grids (e.g., one or more short edges formed by the boundary pixels as described in 1206).

In some embodiments, the grid division of a region may employ a grid generation technique based on parallel operations. For example, a region division or similar algorithm may be employed to divide the region into multiple subregions. Each of the sub-regions may be independently divided into grids. Then, the boundary grids of adjacent sub-regions may be modified to obtain complete grids of the region.

In 1214, a grid division control condition may be set for the region. In some embodiments, the setting of the grid division control condition may be implemented by the grid generation unit 540. The grid division control condition may control grid count, size, distribution, shape, or the like, or one or more combinations thereof. In some embodiments, the grid generation unit 540 may set an area constraint condition for a grid to limit the area of any grid in the region. For example, the grid generation unit 540 may set an area constraint value such that the area of any grid is not larger than the area constraint value. In some embodiments, the grid generation unit 540 may set an interior angle constraint condition for a grid such that the interior angle of any grid satisfies the interior angle constraint condition. For example, the grid generation unit 540 may set an interior angle constraint value for a triangular grid such that the minimum internal angle of any triangular grid is not less than the inner angle constraint value. In some embodiments, the grid division control condition may be obtained by a user via, for example, the communication device 140. The grid division control condition may also be obtained by the grid generation unit 540 or other unit/module with a data analysis function according to analysis of specific conditions. The specific conditions may include the time needed to generate the grids, the number of the generated grids, the time of model computation based on the generated grids, an accuracy degree of the obtained result based on the generated grids, etc.

In 1216, whether the divided grid satisfies the control condition may be determined. In some embodiments, the determination of the grid division may be implemented by the grid generation unit 540. In response to the determination that the divided grid does not satisfy the control condition, the process 1200 may proceed to 1218.

In 1218, the grid may be processed. In some embodiments, processing the grid may be implemented by the grid generation unit 540. The grid processing may include one or more operations such as adjusting the number of grids, changing the size(s) of the grids, etc. Adjusting the number of grids may include increasing grid density, reducing grid density, etc. Changing the size of the grid may include segmenting the grid, merging the grid, reorganizing the grid, etc.

In some embodiments, if a triangular grid does not satisfy the area constraint condition (for example, the area of the triangular mesh cell is greater than the area constraint value), one or more auxiliary points may be inserted in the triangular grid. The auxiliary points may be inserted randomly, or be inserted according to the position of the feature points of the original triangular grid. The grid generation unit 540 may generate a new grid based on the auxiliary points. For example, an auxiliary point may be inserted inside the triangular grid, e.g., t at the center of gravity of the triangular grid. Connecting the auxiliary point and vertices of the original triangular grid may generate three new triangular grids. As another example, a plurality of auxiliary points may be inserted randomly or non-randomly in the triangular gird cell. A Delaunay triangular grid may be divided by employing the Delaunay triangular division algorithm according to the multiple auxiliary points. In some embodiments, if a triangular grid does not satisfy an interior angle constraint, a specific algorithm may be employed to process the triangular grid. For example, a flip algorithm may be employed to update the triangular grid. More particularly, the flip algorithm may include selecting a quadrilateral containing two adjacent triangular grids (i.e., a diagonal line of the quadrilateral is the adjacent edge of the two triangular grids); selecting another diagonal line as the adjacent edge of two new triangular grids; and obtaining two new triangular grids. The inner angle constraint condition may include that the minimum interior angle of the triangular grid unit is not less than an inner angle constraint value. The inner angle constraint value may be 5°, 10°, 15°, 20°, 25°, etc.

The processed grid may return to 1216. The grid generation unit 540 may determine whether the processed grid satisfies a control condition. Until the grid satisfies the control condition, process 1200 may proceed to 1220.

In 1220, the grid generation unit 540 may determine whether all regions have been analyzed. For example, the analysis of the regions may include determining whether the regions needs a grid division. In response to the determination that not all regions have been analyzed, process 1200 may return to 1208 to determine whether the remaining unanalyzed regions need to be grid divided. In response to the determination that all regions have been analyzed, grids of the interesting region may be generated by the grid generation unit 540 in 1222. In some embodiments, algorithms that employed by grid division of different regions may be the same or different. For example, all regions may employ the Delaunay triangular division algorithm for grid division. For example, a part of the regions may employ the Delaunay triangular division algorithm for grid division, and other part of regions may employ a quadrilateral grid algorithm or a hexagonal grid algorithm for grid division. In some embodiments, the grid division control conditions of different regions may be the same or different. For example, the grid control conditions of all regions may include area constraint conditions and/or interior angle constraints. The area constraint controls and/or the interior angle constraints of different areas may be the same or different. More particularly, the interior angle constraint condition of all regions may include that the minimum internal angle of any triangular grid is not less than an inner angle constraint value (e.g., 20°). As another example, the area constraint condition of a brain image may include that an area of the largest triangular grid is not greater than A, and the area constraint condition of the vascular image may include that the area of the largest triangular grid is not greater than B, wherein A is smaller than B.

The above description of the present disclosure is provided for purposes of illustration, and not intended to limit the scope of the present disclosure. For persons having ordinary skills in the art, modules may be combined in various ways, or connected with other modules as subsystems. Various variations and modifications may be conducted under the teaching of the present disclosure. However, those variations and modifications may not depart the spirit and scope of this disclosure. In some embodiments, 1210 may be omitted. In some embodiments, 1214 may be performed before 1208, i.e., the grid generation unit 540 may set the same grid division control conditions for all regions that needs a grid division. In some embodiments, the process 1200 may divide a 3-dimensional image into grids. For example, the grid division of the 3-dimensional region may employ a fast Delaunay based sphere packing technique. The grid generation unit 540 may generate nodes of grids in a 3-dimensional geometric region by filling based on the sphere packing technique. The nodes may be generated with appropriate density according to the geometric features and spatial relations of the geometric model. Then a 3-dimensional grid may be generated by employing the fast Delaunay insertion technique.

Figure 13:
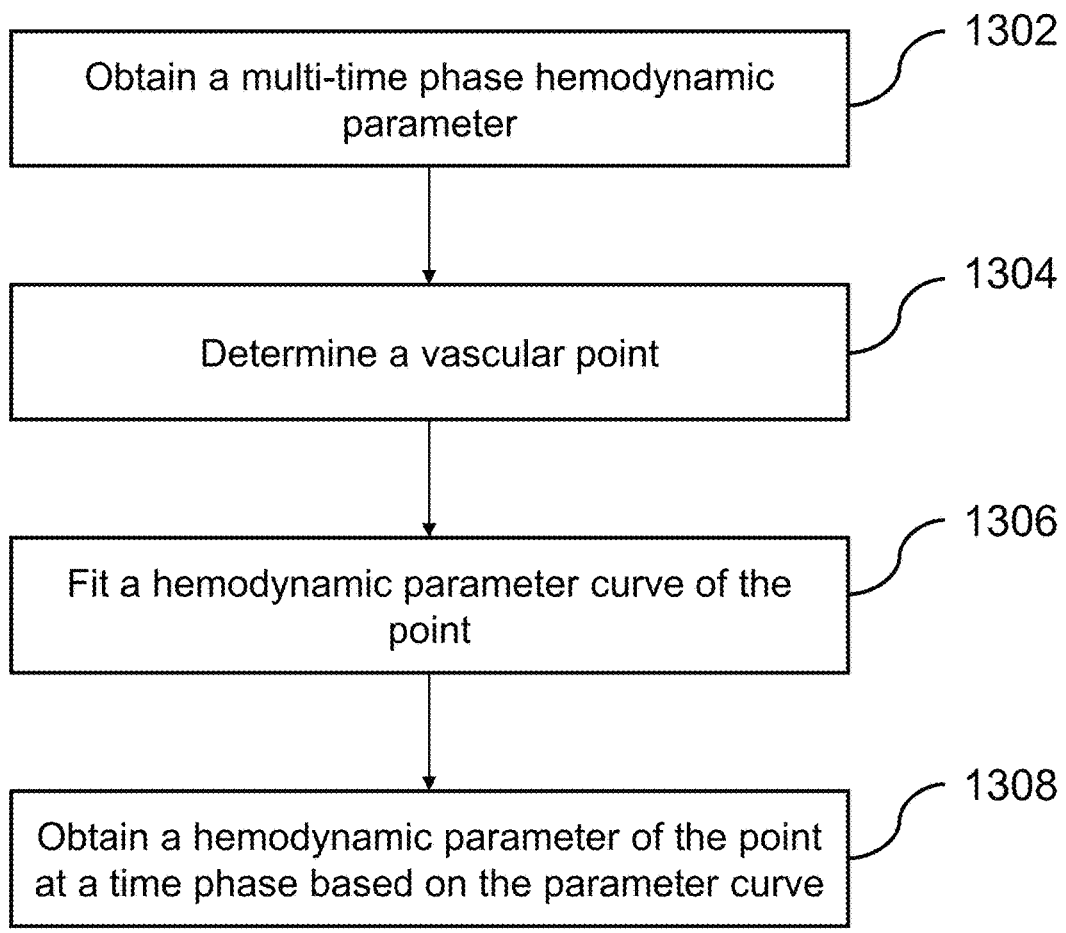
FIG. 13 illustrates a flow chart of a process for obtaining hemodynamic parameters corresponding to a point according to some embodiments of the present disclosure.

FIG. 13 illustrates a flow chart of a process for obtaining hemodynamic parameters corresponding to a point according to some embodiments of the present disclosure. In some embodiments, process 1300 may be implemented by the multi-time phase feature processing module 440. In some embodiments, 468 in FIG. 4B may be implemented based on the process 1300.

In 1302, the multi-time phase feature processing module 440 may obtain a multi-time phase hemodynamic parameter. In some embodiments, the multi-time phase hemodynamic parameter may be related to 614 through 618 in process 600. The hemodynamic parameter may represent the blood flow condition of a vascular region, such as the vascular region of a coronary artery, an abdominal artery, a brain artery, a lower extremity artery, etc. The hemodynamic parameter may include blood velocity, blood pressure, wall stress of the blood vessel, wall shear stress (WSS) of the blood vessel, fractional flow reserve (FFR), coronary flow reserve (CFR), or the like, or any combination thereof. In some embodiments, the multi-time phase hemodynamic parameter value may correspond to a blood flow condition in a specific time period. For example, the hemodynamic parameter at different phases in a cardiac cycle may be obtained such that the blood flow condition in the cardiac cycle may be obtained. Number of the obtained time phases may be 3, 5, 8, 10, 15, etc.

In 1304, the multi-time phase feature processing module 440 may determine a point. The point may be an arbitrary point on the surface of a vascular entrance/exit, or an arbitrary point on the vascular wall or internal space of a blood vessel. In some embodiments, the point may be determined by a user via, for example, the communication device 140.

In 1306, the multi-time phase feature processing module 440 may interpolate the hemodynamic parameter curve of the point. In some embodiments, the hemodynamic parameter curve may represent a blood flow condition within a cardiac cycle. The interpolation may include fitting the multi-time phase hemodynamic parameters based on a function. The function may be linear or non-linear. Suitable non-linear functions may include a polynomial function, a logarithmic function, an exponential function, or the like, or any combination thereof. For example, according to a multi-time phase FFR value of a point on the surface of a coronary entrance, an FFR curve of the point within a certain time range may be obtained. After obtaining the FFR fitting curve of the point in a cardiac cycle, an FFR curve of the point at any time may further be generated according to the periodicity of the heart beating.

In 1308, the multi-time phase feature processing module 440 may obtain the value of a hemodynamic parameter (e.g., an FFR value) of a point at a time phase of interest based on the parameter curve. The time phase of interest may be different from the multiple time phases obtained in 1302. In some embodiments, the selection of the time phase of interest may be implemented by a user via, for example, the communication device 140. In some embodiments, the multi-time phase feature processing module 440 may process the hemodynamic parameter values of the point based on the hemodynamic parameter curve. For example, an average hemodynamic parameter value (e.g., an average FFR value) may be obtained based on the values of hemodynamic parameters (e.g., FFR values) during a period of time.

The above description of the present disclosure is provided for purposes of illustration, and not intended to limit the scope of the present disclosure. For persons having ordinary skills in the art, modules may be combined in various ways, or connected with other modules as subsystems. Various variations and modifications may be conducted under the teaching of the present disclosure. However, those variations and modifications may not depart the spirit and scope of this disclosure. For example, before simulating a curve of hemodynamic parameters of a point, the multi-time phase feature processing module 440 may obtain extra hemodynamic parameters of the point. The extra hemodynamic parameters may be obtained by an interpolation method, or by a user via the communication device 140.

Figure 14:
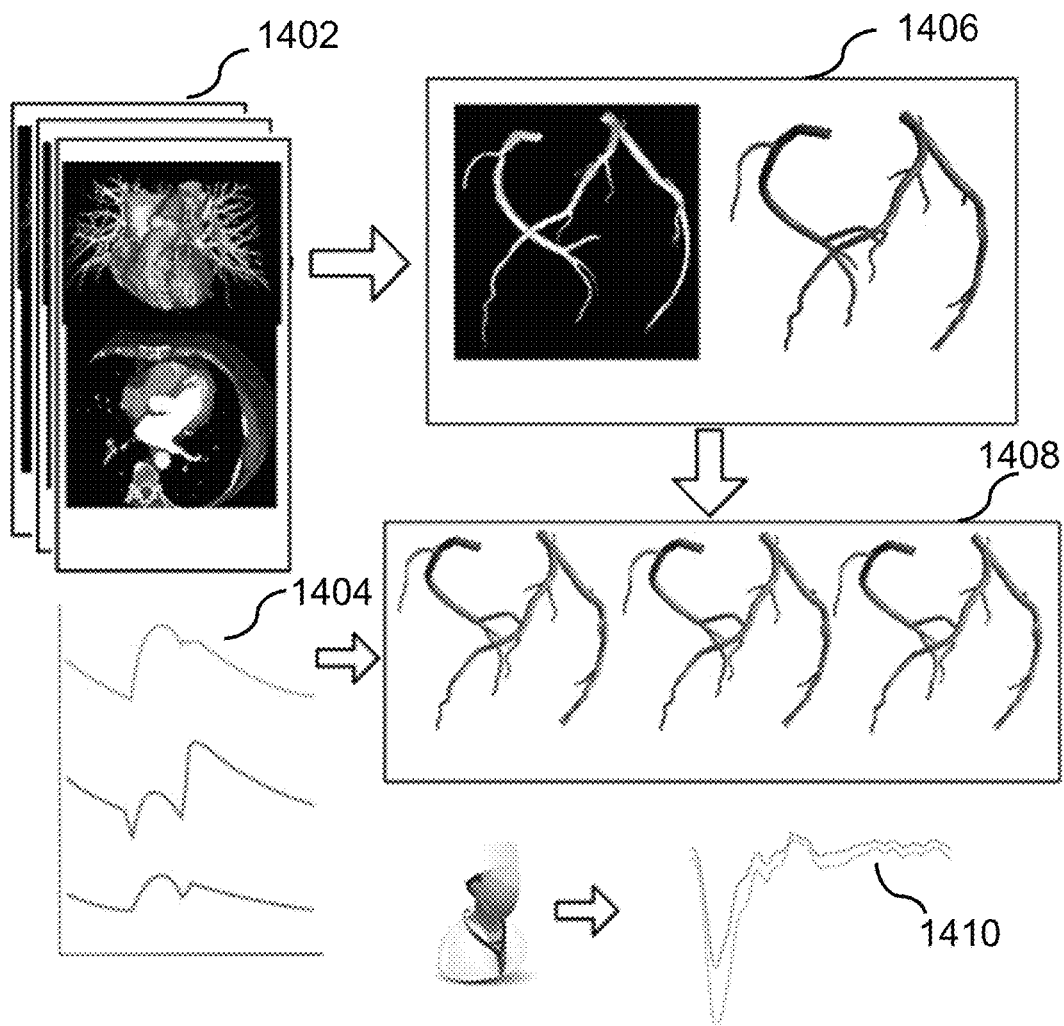
FIG. 14 illustrates a schematic diagram of a process for obtaining a hemodynamic parameter corresponding to a point according to some embodiments of the present disclosure.

FIG. 14 illustrates a schematic diagram of a process for obtaining a hemodynamic parameter corresponding to a point according to some embodiments of the present disclosure. Image 1402 may illustrate multi-time phase image data including a heart region and an abdominal region. Image 1406 may illustrate a coronary artery and a constructed coronary artery model corresponding to an image at the same time phase. Image 1408 may illustrate an FFR distribution of the coronary artery at different time phases. Blood flow conditions at the different time phases may be obtained in the process 600. Image 1404 may illustrate specific clinical data of an object, including a curve of the aortic pressure varying with time, and a curve of the phase coronary blood flow varying with time. Image 1410 may illustrate a curve of the FFR of the object varying with time.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
a storage device including a set of instructions for analyzing blood flow conditions; and
at least one processor in communication with the storage device, wherein when executing the set of instructions, the at least one processor is configured to cause the system to:
obtain vascular images at multiple time phases, including a first vascular image at a first time phase and a second vascular image at a second time phase, wherein the vascular images at multiple time phases correspond to a same blood vessel or a part thereof;
generate multiple vascular models, wherein the multiple vascular models correspond to the vascular images at multiple time phases;
obtain, according to the multiple vascular models, multiple conditions of the blood vessel or the part thereof including a first vascular condition and a second vascular condition, wherein the first vascular condition corresponds to the first vascular image, and the second vascular condition corresponds to the second vascular image;
determine, according to the multiple conditions of the blood vessel or the part thereof, a relationship between condition of the blood vessel or the part thereof and time phase; and
obtain, according to the relationship, a third vascular condition of the blood vessel or the part thereof at a third time phase.

2. The system of claim 1, wherein the blood vessel comprises at least one of a coronary artery, an abdominal artery, a cerebral artery, or a lower extremity artery.

3. The system of claim 1, wherein the multiple conditions of the blood vessel or the part thereof comprises at least one of blood velocity, blood pressure, wall stress of the blood vessel, wall shear stress (WSS) of the blood vessel, fractional flow reserve (FFR), or coronary flow reserve (CFR).

4. The system of claim 1, wherein the third vascular condition comprises an average fractional flow reserve (FFR).

5. The system of claim 1, wherein the at least one processor is further configured to cause the system to:
correlate the multiple vascular models; and
determine the multiple conditions of blood vessels by employing a technique of computational fluid dynamics (CFD) according to the correlation.

6. The system of claim 5, wherein to correlate the multiple vascular models, the at least one processor is further configured to cause the system to correlate at least two of the multiple vascular models at an entrance, a bifurcation segment, a stenosis segment, or an exit of the blood vessel or the part thereof.

7. The system of claim 1, wherein the at least one processor is further configured to cause the system to:
generate grids of the multiple vascular models respectively; and
match the grids of the multiple vascular models.

8. The system of claim 1, wherein the relationship between condition of the blood vessel or the part thereof and time phase is represented by a curve or in a table.

9. The system of claim 1, wherein the vascular images at multiple time phases are cardiovascular images obtained in one or more cardiac cycles.

10. The system of claim 1, wherein the first time phase corresponds to a systole in a cardiac cycle, the second time phase corresponds to a diastole in the cardiac cycle, and the third time phase corresponds to a time phase in the cardiac cycle.

11. A method implemented on a computing device having at least one storage device storing a set of instructions for analyzing blood flow conditions, and at least one processor in communication with the at least one storage device, the method comprising:
obtaining vascular images at multiple time phases, including a first vascular image at a first time phase and a second vascular image at a second time phase, wherein the vascular images at multiple time phases correspond to a same blood vessel or a part thereof;
generating multiple vascular models, wherein the multiple vascular models correspond to the vascular images at multiple time phases;
obtaining, according to the multiple vascular models, multiple conditions of the blood vessel or the part thereof, including a first vascular condition and a second vascular condition, wherein the first vascular condition corresponds to the first vascular image, and the second vascular condition corresponds to the second vascular image;
determining, according to the multiple conditions of the blood vessel or the part thereof, a relationship between condition of the blood vessel or the part thereof and time phase; and
obtaining, according to the relationship, a third vascular condition of the blood vessel or the part thereof.

12. The method of claim 11, wherein the blood vessel comprises at least one of a coronary artery, an abdominal artery, a cerebral artery, or a lower extremity artery.

13. The method of claim 11, wherein the multiple conditions of the blood vessel or the part thereof comprises at least one of blood velocity, blood pressure, wall stress of the blood vessel, wall shear stress (WSS) of the blood vessel, fractional flow reserve (FFR), or coronary flow reserve (CFR).

14. The method of claim 11, wherein the third vascular condition comprises an average fractional flow reserve (FFR).

15. The method of claim 11, further comprising:
correlating the multiple vascular models; and
determining the multiple conditions of blood vessels by employing a technique of computational fluid dynamics (CFD) according to the correlation.

16. The method of claim 15, wherein the correlating the multiple vascular models comprises correlating at least two of the vascular models at an entrance, a bifurcation segment, a stenosis segment, or an exit of the blood vessel or the part thereof.

17. The method of claim 11, further comprising:
generating grids of the multiple vascular models respectively; and
matching the grids of the multiple vascular models.

18. The method of claim 11, wherein the relationship between the condition of the blood vessel or the part thereof and time phase is represented by a curve or in a table.

19. The method of claim 11, wherein the vascular images at multiple time phases are cardiovascular images obtained in one or more cardiac cycles.

20. A non-transitory computer readable medium, comprising executable instructions for analyzing blood flow conditions that, when executed by at least one processor of an electronic device, direct the at least one processor to perform actions of:

obtaining vascular images at multiple time phases, including a first vascular image at a first time phase and a second vascular image at a second time phase, wherein the vascular images at multiple time phases correspond to a same blood vessel or a part thereof;

generating multiple vascular models, wherein the multiple vascular models correspond to the vascular images at multiple time phases;

obtaining, according to the multiple vascular models, multiple conditions of the blood vessel or the part thereof, including a first vascular condition and a second vascular condition, wherein the first vascular condition corresponds to the first vascular image, and the second vascular condition corresponds to the second vascular image;

determining, according to the multiple conditions of the blood vessel or the part thereof, a relationship between condition of the blood vessel or the part thereof and time phase; and obtaining, according to the relationship, a third vascular condition of the blood vessel or the part thereof.

\* \* \* \* \*